(12) United States Patent
Burrowes et al.

(10) Patent No.: US 9,687,867 B2
(45) Date of Patent: Jun. 27, 2017

(54) DISPENSERS FOR DISPENSING MICROCAPSULES

(71) Applicant: The Procter & Gamble Company, Cincinnati, OH (US)

(72) Inventors: Lee Burrowes, Horsell (GB); William John Cleveland Connolly, Windlesham (GB); Andrew Graham Masters, Ruislip (GB); James Samuel Richardson, Morden (GB)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/848,845

(22) Filed: Sep. 9, 2015

(65) Prior Publication Data

US 2017/0065995 A1 Mar. 9, 2017

(51) Int. Cl.
*B05B 1/00* (2006.01)
*B05B 11/00* (2006.01)
*A61L 9/14* (2006.01)
*B05B 1/34* (2006.01)

(52) U.S. Cl.
CPC .......... *B05B 11/3081* (2013.01); *A61L 9/14* (2013.01); *B05B 11/3001* (2013.01); *B05B 11/3047* (2013.01); *B05B 11/3057* (2013.01); *B05B 11/3084* (2013.01); *B05B 1/341* (2013.01); *B05B 11/0037* (2013.01)

(58) Field of Classification Search
CPC ........ B05B 1/341; B05B 11/3081; A61L 9/14
USPC .......................................... 239/304, 399, 463
See application file for complete search history.

(56) References Cited

U.S. PATENT DOCUMENTS

| 3,236,418 A | 2/1966 | Dalle et al. |
| 3,488,004 A | 1/1970 | Peeps |
| 4,826,048 A * | 5/1989 | Skorka ................ B67D 7/0205 |
| | | 222/135 |
| 5,152,461 A | 10/1992 | Proctor |

(Continued)

FOREIGN PATENT DOCUMENTS

| DE | 3911089 | 10/1990 |
| EP | 1 176 945 B1 | 11/2004 |

(Continued)

OTHER PUBLICATIONS

Patchan et al., Liquid-Filled Metal Microcapsules, The Johns Hopkins University, American Chemical Society, Applied Materials & Interfaces, 2012, 4, pp. 2406-2412.

(Continued)

*Primary Examiner* — Arthur O Hall
*Assistant Examiner* — Viet Le
(74) *Attorney, Agent, or Firm* — Betty J. Zea

(57) ABSTRACT

A dispenser for applying at least two compositions, the dispenser including at least two reservoirs for storing the at least two compositions separately, at least two pumps for pumping the at least two compositions, an optional premix chamber for mixing the two compositions before dispensing, at least two channels for delivering the compositions from the reservoirs to the premix chamber or swirl chamber, an exit orifice, an actuator, and a lever assembly for reducing the actuation force required to activate the two pumps; wherein the first composition includes microcapsules and the second composition includes a volatile solvent.

13 Claims, 7 Drawing Sheets

(56) References Cited

U.S. PATENT DOCUMENTS

| | | | |
|---|---|---|---|
| 5,169,029 A | 12/1992 | Behar et al. | |
| 5,332,157 A | 7/1994 | Proctor | |
| 5,901,883 A | 5/1999 | Ritsche | |
| 5,967,372 A | 10/1999 | Favre | |
| 6,082,588 A | 7/2000 | Markey et al. | |
| 6,189,810 B1 | 2/2001 | Nerushai et al. | |
| 6,341,717 B2 * | 1/2002 | Auer | 222/135 |
| 6,454,135 B1 * | 9/2002 | Brozell | B05B 11/3011 222/135 |
| 6,626,379 B1 | 9/2003 | Ritsche et al. | |
| 6,655,551 B2 | 12/2003 | Manne | |
| 6,672,483 B1 | 1/2004 | Roy | |
| 6,722,532 B2 | 4/2004 | Lasserre et al. | |
| 6,869,027 B2 | 3/2005 | Foster et al. | |
| 6,978,946 B2 | 12/2005 | Sweeton | |
| 7,021,499 B2 | 4/2006 | Hansen et al. | |
| 7,335,631 B2 | 2/2008 | McDermott et al. | |
| 7,594,594 B2 | 9/2009 | Troost et al. | |
| 7,775,401 B2 | 8/2010 | Banco et al. | |
| 7,798,366 B2 | 9/2010 | Hoshino | |
| 7,819,342 B2 | 10/2010 | Spallek et al. | |
| 7,832,654 B2 | 11/2010 | Xu et al. | |
| 7,875,001 B2 | 1/2011 | Minotti | |
| 7,906,473 B2 | 3/2011 | Williams et al. | |
| 7,967,220 B2 | 6/2011 | Hansen et al. | |
| 7,997,449 B2 | 8/2011 | Banco et al. | |
| 8,338,354 B2 | 12/2012 | Williams et al. | |
| 8,784,504 B2 | 7/2014 | Williams et al. | |
| 9,186,642 B2 | 11/2015 | Dihora et al. | |
| 9,303,820 B2 | 4/2016 | Miller | |
| 2004/0256490 A1 | 12/2004 | Sweeton | |
| 2005/0226900 A1 | 10/2005 | Winton Brooks et al. | |
| 2005/0258192 A1 * | 11/2005 | Matthews | A47K 5/14 222/190 |
| 2006/0205617 A1 | 9/2006 | Holzner et al. | |
| 2006/0207596 A1 | 9/2006 | Lane | |
| 2006/0258768 A1 | 11/2006 | Uchiyama et al. | |
| 2010/0091478 A1 | 4/2010 | Miller | |
| 2011/0186596 A1 | 8/2011 | Fontana | |
| 2015/0351519 A1 | 12/2015 | Dring et al. | |
| 2015/0352575 A1 | 12/2015 | Dring et al. | |
| 2015/0352576 A1 | 12/2015 | Burrowes et al. | |
| 2015/0352577 A1 | 12/2015 | Burrowes et al. | |
| 2015/0352578 A1 | 12/2015 | Burrowes et al. | |
| 2015/0352579 A1 | 12/2015 | Burrowes et al. | |
| 2015/0353867 A1 | 12/2015 | Dring et al. | |
| 2015/0354550 A1 | 12/2015 | Burrowes et al. | |
| 2015/0375245 A1 | 12/2015 | Burrowes et al. | |

FOREIGN PATENT DOCUMENTS

| | | |
|---|---|---|
| FR | 2 669 243 B1 | 2/1993 |
| JP | 4464803 B2 | 5/2010 |

OTHER PUBLICATIONS

PCT International Search Report dated May 24, 2016—4 pages.
All Office Actions U.S. Appl. No. 14/848,816.
All Office Actions U.S. Appl. No. 14/848,880.
All Office Actions U.S. Appl. No. 14/848,921.

* cited by examiner

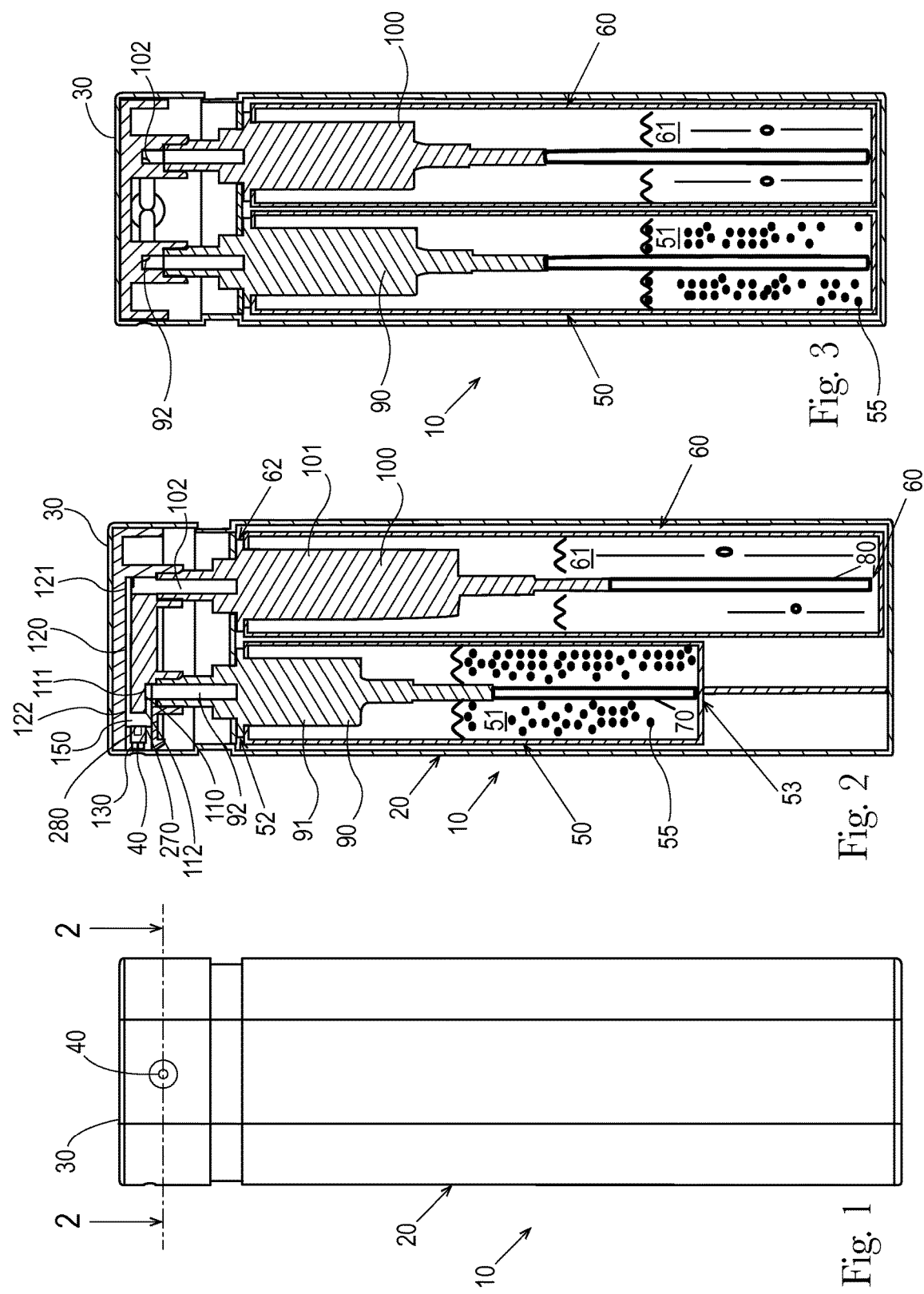

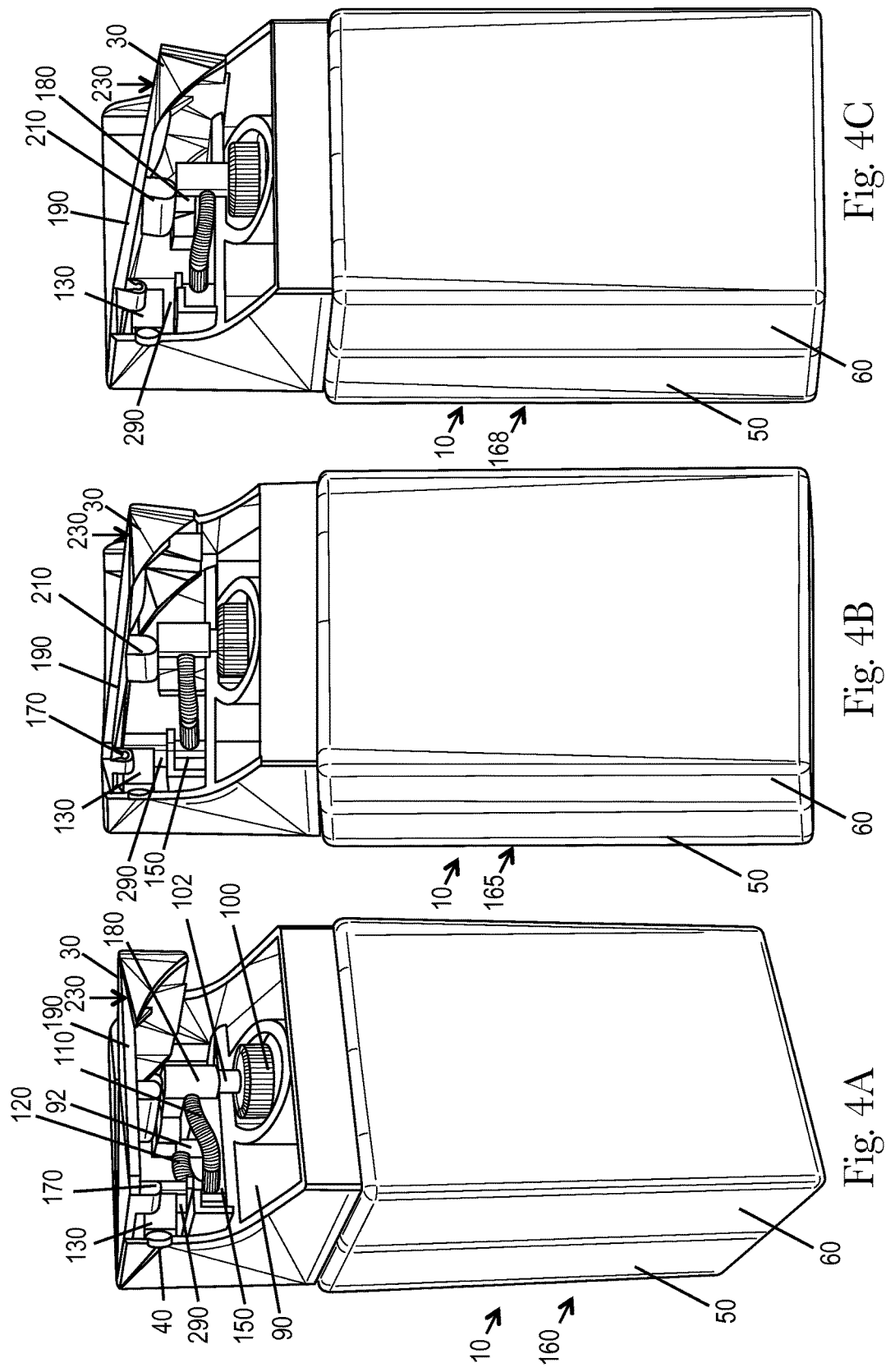

US 9,687,867 B2

DISPENSERS FOR DISPENSING MICROCAPSULES

TECHNICAL FIELD

The present disclosure generally relates to a dispenser for dispensing a volatile solvent and microcapsules stored in separate reservoirs.

BACKGROUND

Consumers often desire to deliver pleasant fragrances during and/or after application of a product. Such fragrances often contain perfume oils and/or other odoriferous materials that provide a scent for a limited period of time. It is also not uncommon to include a solvent for solubilizing the perfumes oils and/or other odoriferous materials. At times, such solvents may be incompatible with other ingredients that may provide a benefit to the consumer. While dispensers that contain separate chambers for separating incompatible ingredients may exist, such dispensers may not be suitable for application in a fine fragrance context. Thus, there exists a need for dispensers that can keep some incompatible ingredients separate while delivering a suitable experience to the consumer.

SUMMARY

A dispenser (10) comprising a first reservoir (50), the first reservoir (50) comprising a first pump (90) and a first composition (51); a second reservoir (60), the second reservoir (60) comprising a second pump (100) and a second composition (61); a first channel (110) having a proximal end (111) and a distal end (112); a second channel (120) having a proximal end (121) and a distal end (122); an exit orifice (40); a swirl chamber (130); and a lever assembly (190), the lever assembly (190) comprising an actuator (30) operatively associated with a pivot providing structure (170); wherein the proximal end (111) of the first channel (110) is in liquid communication with the first pump (90) and the distal end (112) of the first channel (110) is in liquid communication with the swirl chamber (130); wherein the proximal end (121) of the second channel (120) is in liquid communication with the second pump (100) and the distal end (122) of the second channel (120) is in liquid communication with the swirl chamber (130); wherein the swirl chamber (130) is in liquid communication with the exit orifice (40); wherein the lever assembly (190) is operatively associated with the first pump and the second pump; wherein the first composition (51) comprises a plurality of microcapsules and the second composition (61) comprises a volatile solvent. A method of providing a longer lasting fragrance, the method comprising spraying a first and second composition using the aforementioned dispenser.

BRIEF DESCRIPTION OF THE DRAWINGS

While the specification concludes with claims, it is believed that the same will be better understood from the following description taken in conjunction with the accompanying drawings in which:

FIG. 1 is a front view of a dispenser;
FIG. 2 is a cross sectional view of the side of a dispenser;
FIG. 3 is a cross sectional view of the front of a dispenser;
FIG. 4A is a cross sectional view of a dispenser having a lever assembly and in a first position;
FIG. 4B is a cross sectional view of the dispenser of FIG. 4A in a second position;
FIG. 4C is a cross sectional view of the dispenser of FIG. 4A in a third position.

DETAILED DESCRIPTION

Figure 5C:
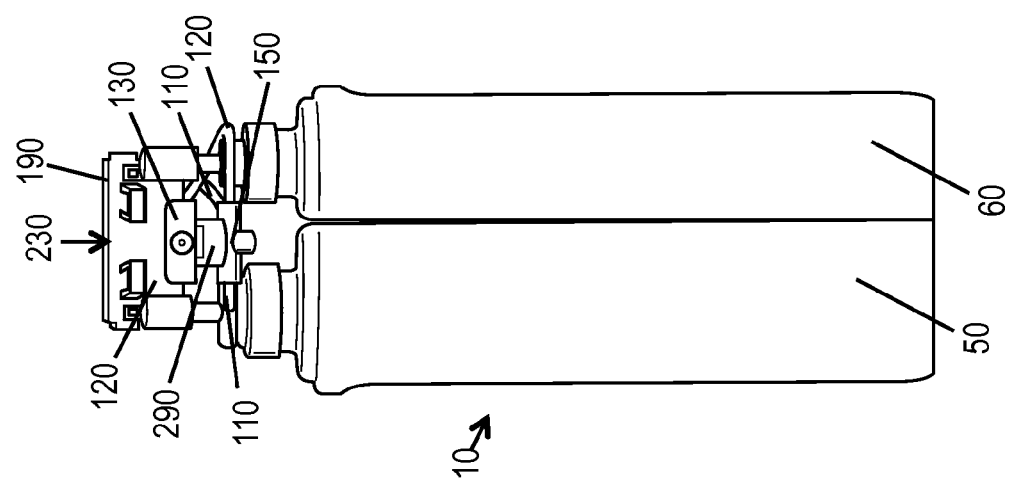
FIG. 5C is a front view of a partial dispenser having a lever assembly.
Figure 5B:
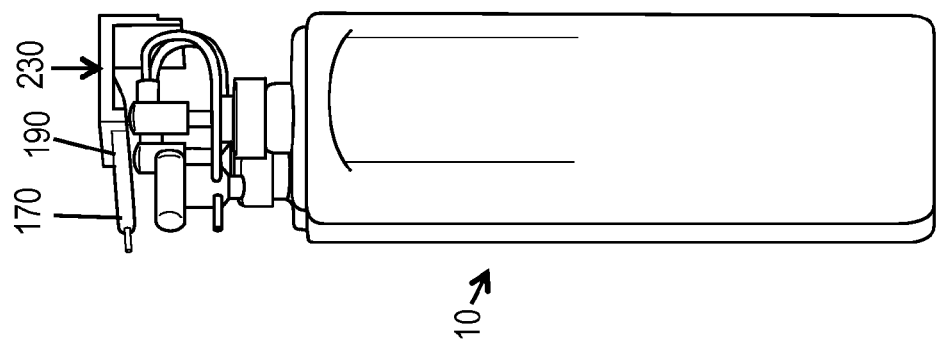
FIG. 5B is a perspective view of the side of a dispenser having a lever assembly.
Figure 5A:
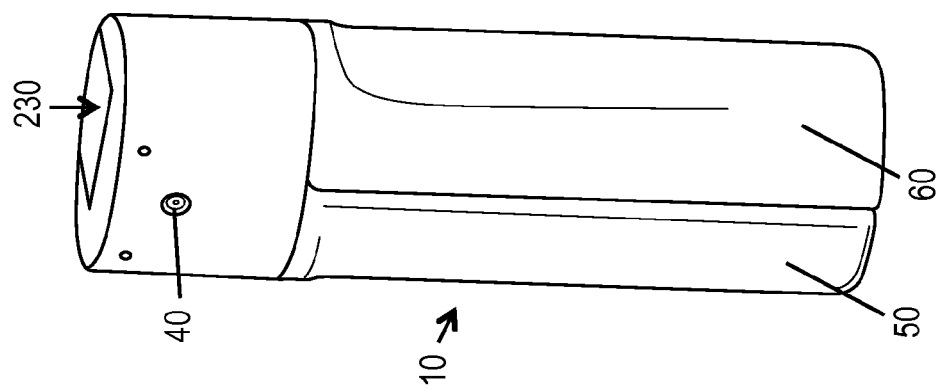
FIG. 5A is a perspective, front view of a dispenser having a lever assembly.
Figure 5D:
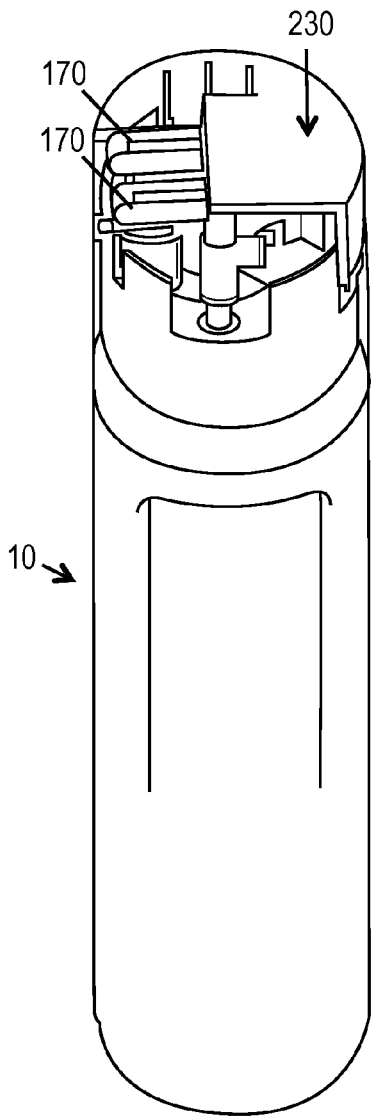
FIG. 5D is a top view of a dispenser having a lever assembly and a partially transparent top.

All percentages are weight percentages based on the weight of the composition, unless otherwise specified. All ratios are weight ratios, unless specifically stated otherwise. All numeric ranges are inclusive of narrower ranges; delineated upper and lower range limits are interchangeable to create further ranges not explicitly delineated. The number of significant digits conveys neither limitation on the indicated amounts nor on the accuracy of the measurements. All measurements are understood to be made at about 25° C. and at ambient conditions, where "ambient conditions" means conditions under about one atmosphere of pressure and at about 50% relative humidity.

"Composition" as used herein, means ingredients suitable for topical application on mammalian keratinous tissue. Such compositions may also be suitable for application to textiles or any other form of clothing including, but not limited to, clothing made from synthetic fibers like nylons and polyesters, and clothing made from acetate, bamboo, cupro, hemp, flannel, jute, lyocell, PVC-polyvinyl chloride, rayon, recycled materials, rubber, soy, Tyvek, cotton, and other natural fibers.

"Exit orifice" herein is shown as a passage from the swirl chamber to the external environment.

"Free of" means that the stated ingredient has not been added to the composition. However, the stated ingredient may incidentally form as a byproduct or a reaction product of the other components of the composition.

"Nonvolatile" refers to those materials that liquid or solid under ambient conditions and have a measurable vapor pressure at 25° C. These materials typically have a vapor pressure of less than about 0.0000001 mmHg, and an average boiling point typically greater than about 250° C.

"Soluble" means at least about 0.1 g of solute dissolves in 100 ml of solvent at 25° C. and 1 atm of pressure.

"Substantially free of" means an amount of a material that is less than 1%, 0.5%, 0.25%, 0.1%, 0.05%, 0.01%, or 0.001% by weight of a composition.

"Derivatives" as used herein, include but are not limited to, amide, ether, ester, amino, carboxyl, acetyl, and/or alcohol derivatives of a given chemical.

"Skin care actives" as used herein, means compounds that, when applied to the skin, provide a benefit or improvement to the skin. It is to be understood that skin care actives are useful not only for application to skin, but also to hair, nails and other mammalian keratinous tissue.

"Volatile," as used herein, unless otherwise specified, refers to those materials that are liquid or solid under ambient conditions and which have a measurable vapor pressure at 25° C. These materials typically have a vapor pressure of greater than about 0.0000001 mmHg, alternatively from about 0.02 mmHg to about 20 mmHg, and an average boiling point typically less than about 250° C., alternatively less than about 235° C.

Fine fragrances, like colognes and parfums, are often desired by consumers for their ability to deliver pleasant scents. A drawback of such fine fragrances is that, because the fragrances are typically volatile, a consumer may have to reapply the fine fragrance after a short period of time in order to keep the same scent expressed. While consumers may desire a fine fragrance product with a longer duration of noticeability, there appears to be no simple solution for extending the duration of noticeability. Hence many fine fragrance products on the market utilize an age old system including a volatile solvent and fragrance oils, said system often offering a short period of noticeability.

One method to increase the duration of noticeability of a fragrance in a product is to incorporate a controlled-release system into the product. In this regard, microcapsules have been included in certain products like deodorants in order to delay the release of a fragrance into the headspace. However, the stability of microcapsules within a composition may be impacted by the ingredients in the composition. For example, some ingredients may cause the microcapsules to be unable to retain their integrity or the encapsulated fragrance to a certain level of degree over time.

It has been observed that the presence of volatile solvents like ethanol in a composition may seriously impact the ability of a fragrance-loaded microcapsule to release its encapsulated fragrance into the headspace. Surprisingly, it has been discovered that minimizing the contact time between the microcapsules and the volatile solvent (e.g. ethanol) allows the microcapsules to deliver a noticeable benefit to a consumer. This can be accomplished by using a dispenser that has at least two reservoirs, one for storing the volatile solvent and the other for storing the microcapsules and their carrier.

Another significant problem that may present itself is that the carrier that may be used for the microcapsules may have a high surface tension such that the composition containing the microcapsules is resistant to atomization. For example when the carrier is water, the high surface tension of water (73 dynes/cm at 20° C.) may resist atomization such that a stream is more likely dispensed rather than a spray. The introduction of a suspending agent for the microcapsules may further exacerbate the problem because the suspending agent may increase the viscosity of the composition containing the water and microcapsules, making it less likely said composition can overcome its relatively high surface tension for atomization. It is well known that compositions having a high surface tension and a high viscosity are difficult to atomize without significant pressure generation. If the composition is not dispensed with sufficient atomization, such a dispenser may not be desirable for a high-end product like a fine fragrance.

Lastly, the dispenser capable of dispensing the microcapsules should not require excessive force for actuation. The amount of force required to active a pump typically consist of two elements: (1) the amount of force required to overcome the resistance of the compression of the pump return spring, and (2) the amount of force required to generate sufficient pressure on the sprayable product inside the pump exit orifice to enable break-up into droplets and create a consumer-desired mist spray. It is, however, possible to activate a pump by only overcoming (1), while not generating sufficient force for (2). This will result in the product leaving the exit orifice with insufficient pressure for break-up and resulting in a jet of product, or in extreme cases simply dribbling out of the exit orifice.

In this regard, consumers are typically well practiced in the process of applying a fine fragrance from standard pumps such that they are aware of the forces required to normally activate a fine fragrance product. However, when a consumer is presented with a dual-pump product, a consumer may be unaware of the need for the application of additional force and may unknowingly apply a force similar to that applied when using a standard fine fragrance product with a single pump. If such a situation occurs, said consumers may experience a non-desirable spray pattern due to the deficient amount of force applied such as by applying enough force to overcome (1) above, but not (2). If the dispenser having two pumps requires too much force to actuate the compositions stored, then such a dispenser may not be desirable for a high-end product like a fine fragrance.

Dispenser

The dispensers herein incorporate a lever assembly advantageously to reduce the actuation force required for a multi-pump design where one composition includes a volatile solvent and the other composition includes microcapsules. The lever provides a mechanical advantage such that a consumer will perceive an actuation force similar to that of standard fine fragrance products with a single pump, while generating sufficient force to generate a desired spray pattern with a dual pump product.

The dispensers described herein also include at least two reservoirs, one for separately storing each of the first and second compositions. The dispensers may also include a swirl chamber for atomizing the two compositions. The first and second compositions preferably exit the dispenser via a common exit orifice. Alternatively, the dispenser may mix the first and second composition via in-flight mixing by utilizing two exit orifices, one for each composition. The dispensers also utilize at least two pumps fitted with pistons, one pump for pumping the first composition and a second pump for pumping the second composition to a swirl chamber and exit orifice.

Preferably, the dispenser may also include a premix chamber, wherein each pump pumps each composition into a channel that serves to deliver the compositions from the reservoirs to a premix chamber. In this regard, the dispensers described herein may first mix the two compositions immediately prior to exit by first mixing the compositions within a premix chamber. The premix chamber may have a volume sufficient to contain from 1% to 75% of the dispensed amount, alternatively from 2% to 20% of the dispensed amount, alternatively from 4% to 14% of the dispensed amount.

The dispensers described herein provide an advantage over those dispensers that have more than one reservoir and retain greater than 75% of the mixture of the two compositions from each reservoir somewhere between the exit orifice and the reservoir when a premix chamber is included. In this regard, dispensers that retain greater than 75% will likely cause the next actuation to yield a mixture containing damaged microcapsules. Limiting the volume of the premix chamber allows for the dispenser to yield a consistent consumer experience as such a design will limit the extent of damaged microcapsules sprayed from the dispenser during each actuation event. The following is a non-limiting example: if the total volume of the dispensed mixture is 105 microliters and the dispensed mixture contains about 35 microliters of the first composition and 70 microliters of the second composition, the premix chamber may have a volume sufficient to mix between 5 microliters and 15 microliters of the first and second compositions combined. In some examples, the premix chamber includes baffles to increase the extent of the mixing within the premix chamber.

Mixing within the premix chamber as described herein provides several advantages. First, the dispensers herein take advantage of the fact that the mixture of certain volatile solvents like ethanol with water results in a mixture with a lower surface tension than water, increasing the likelihood that the two compositions are appropriately aerosolized. Second, by limiting the duration and extent of the mixing, the microcapsules are less likely to be damaged upon exit. Third, limiting the duration and extent of mixing also minimizes potential clogging. Lastly, the designs herein provide a consistent consumer experience by minimizing the amount of residual mixture left within the dispenser after each actuation event.

The size of the dispenser may be such as to allow it to be handheld. The dispenser may include a first composition stored in a first reservoir and a second composition stored in a second reservoir. The second composition may include a volatile solvent and a first fragrance. The first composition may include a plurality of microcapsules and a carrier (e.g. water). The first composition may further include a suspending agent. The first and second compositions may each further include any other ingredient listed herein unless such an ingredient negatively affects the performance of the microcapsules. Non-limiting examples of other ingredients include a coloring agent included in at least one of the first and second compositions and at least one non-encapsulated fragrance in the second composition. When the first composition comprises microcapsules encapsulating a fragrance, the first composition may further include a non-encapsulated fragrance that may or may not differ from the encapsulated fragrance in chemical make-up. In some examples, the first composition may be substantially free of a material selected from the group consisting of a propellant, ethanol, a detersive surfactant, and combinations thereof; preferably free of a material selected from the group consisting of a propellant, ethanol, a detersive surfactant, and combinations thereof. Non-limiting examples of propellants include compressed air, nitrogen, inert gases, carbon dioxide, gaseous hydrocarbons like propane, n-butane, isobutene, cyclopropane, and mixtures thereof. In some examples, the second composition may be substantially free of a material selected from the group consisting of a propellant, microcapsules, a detersive surfactant, and combinations thereof; preferably free of a material selected from the group consisting of propellant, microcapsules, a detersive surfactant, and combinations thereof.

The dispenser may be configured to dispense a volume ratio of the second composition to the first composition at a ratio of from 10:1 to 1:10, from 5:1 to 1:5, from 3:1 to 1:3, from 2:1 to 1:2, or even 1:1 or 2:1, when the second composition comprises a volatile solvent and the first composition comprises a carrier and a plurality of microcapsules, according to the desires of the formulator. The dispenser may dispense a first dose of the second composition and a second dose of the first composition such that the first dose and the second dose have a combined volume of from 30 microliters to 300 microliters, alternatively from 50 microliters to 140 microliters, alternatively from 70 microliters to 110 microliters.

As shown in FIG. 1, the dispenser 10 may have a housing 20, an actuator 30 and an exit orifice 40. In some non-limiting examples, the exit orifice may have a volume of 0.01 cubic millimeters to 0.20 cubic millimeters, such as when the exit orifice 40 has a volume of 0.03 cubic millimeters. In some examples, the housing 20 may not be necessary; a non-limiting example of which is when the reservoirs 50, 60 are made of glass. When the reservoirs are made of glass, the two reservoirs may be blown from the same piece of molten glass, appearing as a single bottle with two reservoirs. Alternatively, when the reservoirs are made of glass, the two reservoirs may be blown from separate pieces of molten glass, appearing as two bottles, each with a single reservoir, and joined together via a connector. One of ordinary skill in the art will appreciate that many possible designs of the reservoirs are possible without deviating from the teachings herein; a non-limiting example of which is a reservoir within a reservoir.

As shown in FIG. 2, the dispenser 10 may also contain a first reservoir 50 for storing a first composition 51 and a second reservoir 60 for storing a second composition 61. The reservoirs 50, 60 may be of any shape or design. The dispenser may be configured to dispense a non-similar volume ratio (not 1:1) of the first composition 51 to the second composition 61, as shown in FIG. 2. The first reservoir 50 may have an open end 52 and a closed end 53. The second reservoir may have an open end 62 and a closed end 63. The open ends 52, 62 may be used to insert the pump and/or dip tubes into the reservoirs. The open ends 52, 62 may also be used to supply the reservoirs with the compositions. Once supplied, the open ends 52, 62 may be capped or otherwise sealed to prevent leakage from the reservoirs. In some examples, the first composition 51 may include microcapsules 55. The dispenser may include a first dip tube 70 and a second dip tube 80, although the dip tubes are not necessary if alternative means are provided for airless communication between the reservoir and the pump, a non-limiting example of which is a delaminating bottle. The dispenser may include a first pump 90 (shown as a schematic) in communication with the first dip tube 70. The dispenser may also include a second pump 100 (shown as a schematic) in communication with the second dip tube 80. The dispenser may also be configured to contain a first pump 90 and a second pump 100 with different output volumes. In some non-limiting examples, at least one pump may have an output of about 70 microliters and the other pump may have an output of about 50 microliters.

As shown in FIG. 2, the first reservoir 50 may be configured to hold a smaller volume than the second reservoir 60 or vice versa when non-similar ratios of the first composition to the second composition are to be dispensed. If dip tubes are included, the first dip tube 70 may also be of a shorter length than the second dip tube 80 or vice versa. The inner workings of the pumps are routine unless otherwise illustrated in the drawings. Such inner workings have been abbreviated and shown as schematic so as to not obscure the details of the teachings herein. Suitable pumps with outputs between 30 microliters to 140 microliter may be obtained from suppliers such as Aptargroup Inc., MeadWeastavo Corp., and Albea. Some examples of suitable pumps are the pre-compression pumps described in WO2012110744, EP0757592, EP0623060.

The first pump 90 may have a chamber 91 and the second pump 100 may have a chamber 101. As illustrated in FIG. 2, the first pump 90 and second pump 100 may be configured so that the chambers 91, 101 have different lengths and similar or the same diameters. The pumps as illustrated herein are in some cases magnified to show the inner details and may be smaller in size than they appear as illustrated herein when said pumps are used for a fine fragrance.

As shown in FIG. 2, the dispenser may include a first channel 110 and a second channel 120. In some non-limiting examples, the channels 110, 120 have a volume of 5 millimeters to 15 millimeters, an example of which is when the channels have a volume of 8.4 cubic millimeters. The first channel 110 may have a proximal end 111 and a distal end 112. The second channel 120 may have a proximal end 121 and a distal end 122. The proximal end 111 of the first channel 110 is in communication with the exit tube 92 of the first pump 90. The proximal end 121 of the second channel 120 is in communication with the exit tube 102 of the second pump 100. The first channel 110 may be of a shorter length as compared to the second channel 120. The second channel 120 may be disposed above the first channel 110 as illustrated in FIG. 2 or below the first channel 110. Alternatively, the first channel and second channel may be substantially coplanar (i.e. exist side-by-side). The exit tubes 92, 102 may have similar or different diameters which can provide for similar or different volumes. In some non-limiting examples, the exit tubes have a diameter of 0.05 millimeters to 3 millimeters, an example of which is when one of the exit tubes has a diameter of 1.4 millimeters and the other exit tube has a diameter of 1 millimeter. In some non-limiting examples, the exit tubes 92, 102 may have a volume of from 2 cubic millimeters to 10 cubic millimeters, such as when one exit tube has a volume of 7.70 cubic millimeters and the other exit tube as a volume of 3.93 cubic millimeters.

To minimize clogging such as may occur when a composition contains particulates (e.g. microcapsules) or displays a different viscosity from the other composition, the channels 110, 120 may be configured such that one of the channels has a larger diameter than the other. The channel with the larger diameter may be used to prevent clogging when particulates are contained within a composition.

The distal end 112 of the first channel 110 and the distal end 122 of the second channel 120 serve to deliver the compositions to separate exit orifices, swirl chamber(s), and/or a premix chamber 150. When a premix chamber 150 is included, the premix chamber 150 may include inner baffles to facilitate mixing. The dispenser may also include at least one feed to deliver the mixture of the first and second composition from the premix chamber 150 to the swirl chamber 130. The swirl chamber 130 may impart on the first composition 51 and the second composition 61 a swirl motion. In some examples, the dispenser may include a first feed 270 in communication with the swirl chamber 130 and the premix chamber 150, as illustrated in FIG. 2. The dispenser may also include a second feed 280 in communication with the swirl chamber 130 and the premix chamber 150. The first feed 270 may be configured to have a different diameter as compared to the second feed 280. Alternatively, the feeds 270, 280 may have a substantially similar diameter. In some examples, the dispenser may have more than two feeds. Alternatively, the dispenser may have a single feed from the premix chamber to the swirl chamber.

The swirl chamber 130 may impart on the first composition 51 and the second composition 61 a swirl motion. The swirl chamber may be configured to deliver certain spray characteristics. For example, the fluid entering the swirl chamber may be provided a swirling or circular motion or other shape of motion within the swirl chamber 130, the characteristics of the motion being driven by the inward design of the swirl chamber 130. In some instances, the mixing of the two compositions in the premix chamber 150 may lower the surface tension of the compositions, and thereby, improving the level of atomization of the liquids. Incorporation of a swirl chamber 130 may further promote atomization when compositions that vary in surface tension and viscosity are present in the reservoirs. It is to be noted that the actual design of the swirl chamber may vary and that one of ordinary skill in the art will recognize that many variations in the design of the swirl chamber are possible. The swirl chamber may be used to impart a swirling motion onto the compositions, said swirling motion promoting the atomization of the compositions for delivery via the exit orifice 40 to the external environment.

Alternatively, the dispenser 10 may be configured to dispense a similar volume ratio (e.g. 1:1) of the first composition 51 to the second composition 61, as shown in FIG. 3. In some examples, the reservoirs 50 and 60 may be of a similar size. The first pump 90 and the second pump 100 may selected to deliver similar outputs. In some examples, the dispenser may be configured so that the chambers 91, 101 have similar or the same diameters while having the same or similar lengths that allow for the same or similar stroke lengths for the pistons. In some examples, the dispenser may be configured so that the reservoir supplying the composition containing the microcapsules is delivered via the longer channel when the channels are of different lengths.

Alternatively, the dispenser may be configured to dispense a non-similar volume ratio (not 1:1) of the first composition 51 to the second composition 6. In some examples, the first pump 90 and second pump 100 may be configured so that the chambers 91, 101 have different diameters while having the same or similar lengths that allow for the same or similar stroke lengths for the pistons, but different pump outputs. Such configurations may deliver in series dispensing of a larger volume of either composition 51, 61 by allowing for pistons of different stroke lengths.

As shown in FIG. 4A, the dispenser 10 also includes a lever assembly 190. The lever assembly 190 includes an actuator 30 with a depressible area 230, wherein the actuator 30 is operatively associated with a pivot providing structure 170 such as a hinge. The pivot providing structure 170 serves as a fulcrum for the lever assembly 190. As shown in FIG. 4B, the lever assembly 190 may be operatively associated with a protrusion 210 that serves to transfer the force applied at the depressible area 230 to a spreader 180. The protrusion 210 may be integral with the lever assembly 190 (as shown) or may be integral with the spreader 180. The protrusion may be rounded on either the top side (as shown) or the bottom side depending on whether it is integral to the lever assembly 190 or the spreader 180.

In some examples, the protrusion 210 may be offset from the center of the spreader 180. Such a configuration may be utilized to distribute a different amount of a force to the pumps. In some examples, the longer arm (as measured from the center point of the spreader 180) of the protrusion 210 may activate the pump pumping the composition containing the microcapsules and the shorter lever arm may activate the pump pumping the composition containing the volatile solvent. Such a design may be advantageous because the composition containing the microcapsules may have a higher viscosity than the composition containing the volatile solvent and more force may be required to pump the composition containing the microcapsules as compared to the composition containing the volatile solvent.

As shown in FIG. 4A, the dispenser 10 may have a first position 160 when no force is being applied to the depressible area 230. As shown in FIG. 4B, upon application of force to the depressible area 230, the dispenser 10 may enter a second position 165 wherein the lever assembly 190 has moved in the direction of the pumps, driving the protrusion 210 to apply force to the spreader 180, resulting in the spreader 180 to move towards the reservoirs 50, 60 causing the first and second pumps to be operative. In some examples, the spreader 180 is operatively associated with plunger of the pumps such that movement of the spreader 180 will cause movement of the plungers within the pumps. While in the second position 165, the first and second compositions are drawn from the pump chambers 91, 101 and into the first and second channels 110, 120 via the first and second pumps 90, 100. In some examples, the first and second channels 110, 120 may deliver the compositions directly to the swirl chamber 130 prior to exit via the exit orifice 40. As shown in FIGS. 4A-4C, in some examples, the first and second channels 110, 120 may deliver the contents to a premix chamber 150 prior to entry into the swirl chamber 130. A feed 290 may be included to deliver the compositions from the premix chamber (150) to the swirl chamber (130). As shown in FIG. 4C, the dispenser 10 may be in a third position 168, the third position resulting from the continued application of force to the depressible area 230 by the user, wherein the first and second pumps enter a resting state such that the first and second pumps are no longer operative and the spreader 180 and depressible area 230 are in a final position relative to the starting position as shown in FIG. 4A.

Figure 5E:
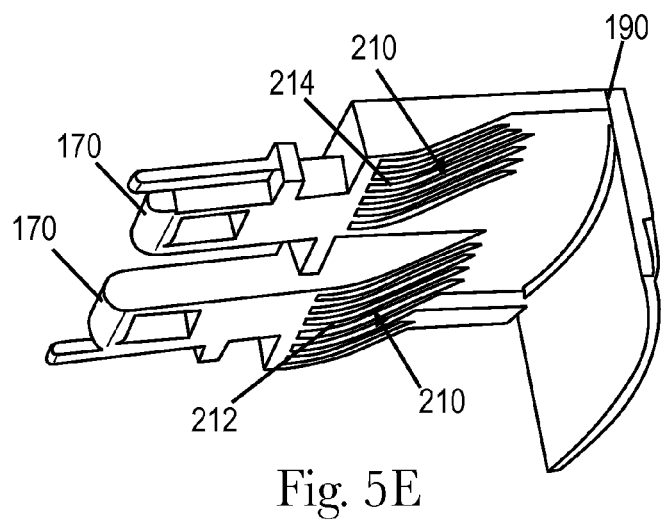
FIG. 5E is a perspective view of a lever assembly.
Figure 5F:
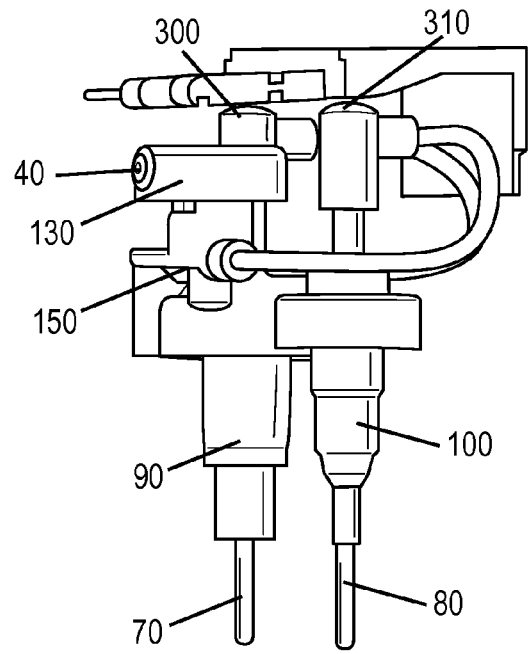
FIG. 5F is a perspective view of an actuator assembly.

As shown in FIGS. 5A-5F, in some examples, the dispenser 10 may include a lever assembly 190 having a protrusion 210 that is integral to the lever assembly 190 and serves to transfer the force applied from the depressible area 230 to the first and second pumps 90,100. The lever assembly 190 includes a pivot providing structure 170 such as a hinge that is integral to the lever assembly 190. As shown in FIG. 5E, the protrusion 210 of the lever assembly 190 may have a first engagement zone 212 and a second engagement zone 214. As shown in FIGS. 5E & 5F, the first engagement zone 212 may be in communication with the first pump contact zone 300 and the second engagement zone 214 may be in communication with second pump contact zone 310 when force is applied to the depressible area 230, leading to activation of the first and second pumps 90,100. In some examples, the first engagement zone 212 may be in physical contact with the first pump contact zone 300 and the second engagement zone 214 may be physical contact with second pump contact zone 310 prior to the application of force to the depressible area 230 such that said physical contact is not sufficient to activate pumps 90, 100.

Figure 6:
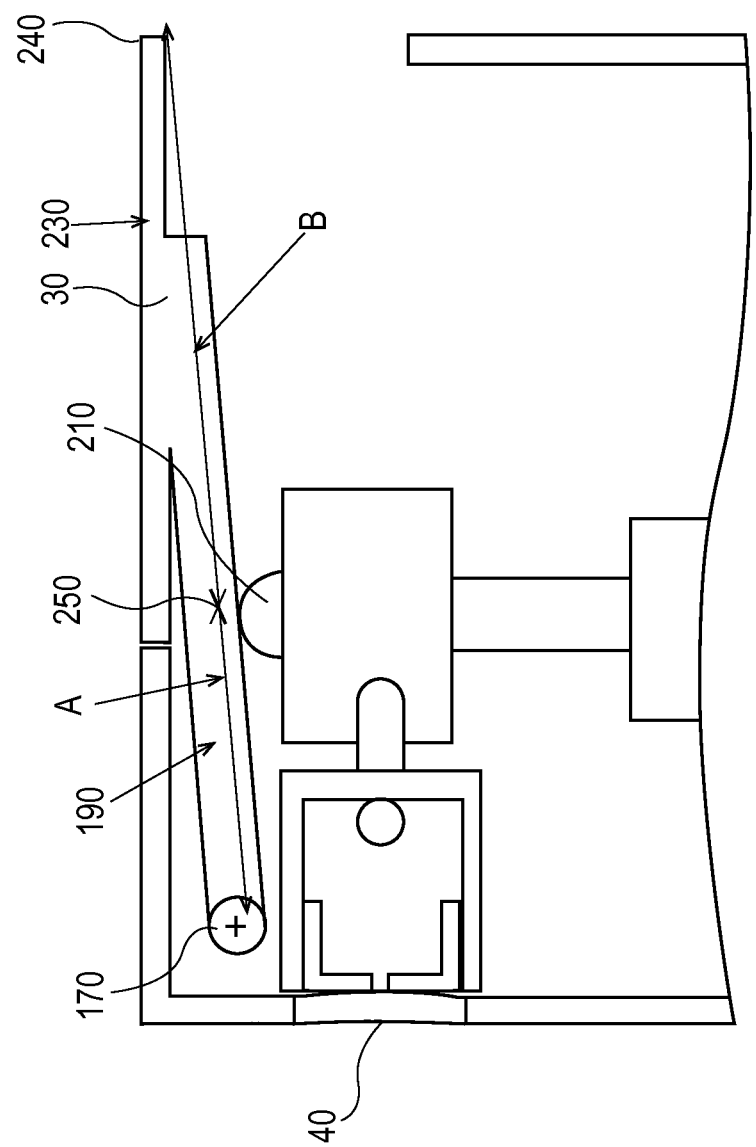
FIG. 6 is schematic of a cross section of a dispenser having a lever assembly.

FIG. 6 demonstrates a simplified schematic to illustrate the theoretical mechanical advantage of the lever designs described herein. The lever assembly 190 may have a total length of A+B from the pivot providing structure 170 (i.e. the pivot point) to the end 240 of the depressible area 230. The length of A is calculated from the pivot point of the pivot providing structure 170 to the force point 250; the force point 250 being the midpoint of where contact is made with the protrusion 210. The length of B is calculated from the force point 250 to the end 240 of the depressible area 230. In some examples, the ratio of A to B is from 10:1 to 1:10, preferably from 5:1 to 1:5, preferably from 3:1 to 1:3, more preferably about 1:1 to about 1:2. In some examples, A has a size of about 10 mm to about 50 mm and B has a size of about 10 mm to about 70 mm such that the length of A+B is about 20 mm to about 120 mm. The theoretical mechanical advantage is defined as the ratio of A+B to A or mathematically expressed as (A+B)/A. FIGS. 4A-4C show a lever assembly 190 with a theoretical mechanical advantage of about 2.8. Thus, the dispenser shown in FIGS. 4A-4C should theoretically require 2.8 times less force to drive the actuator 30 to the third position 168 as compared to a similar dispenser without a lever assembly.

Figure 7:
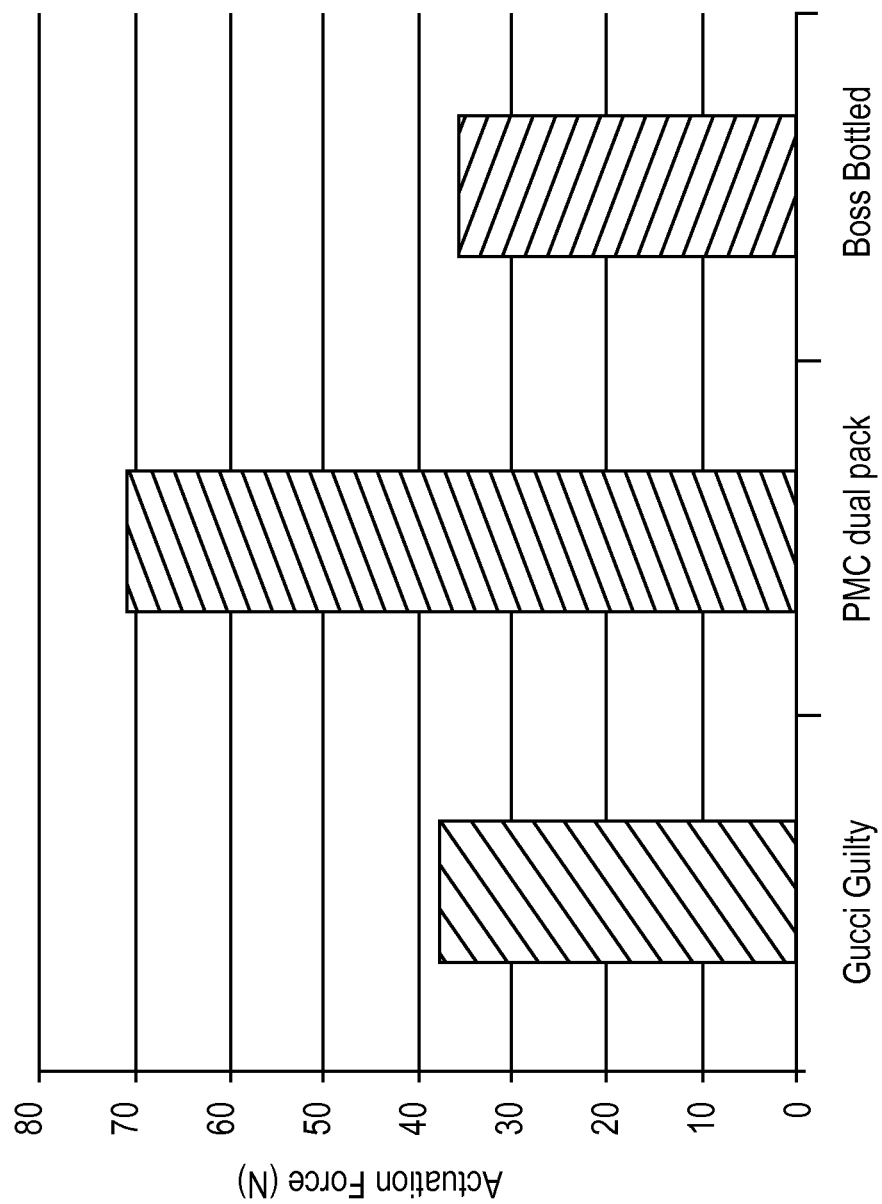
FIG. 7 is a graph comparing the force required to actuate the contents of two known fine fragrance products (Hugo Boss® and Gucci Guilty®) to a dispenser similar to FIG. 1 (labeled "PMC Dual Pack")

As shown in FIG. 7, in-market fine fragrance products such as Gucci Guilty® have an actuation force of from about 30 N to 40 N. The "PMC Dual pack" represents a dual dispenser lacking a lever assembly and including a first composition containing microcapsules and a second composition containing a volatile solvent. Because of the requirement for two pumps, the actuation force required to actuate the two compositions of the "PMC Dual pack" is greater than 70 N. By incorporating the lever design disclosed herein, the actuation force required may be decreased for a dual pump dispenser product.

Figure 8:
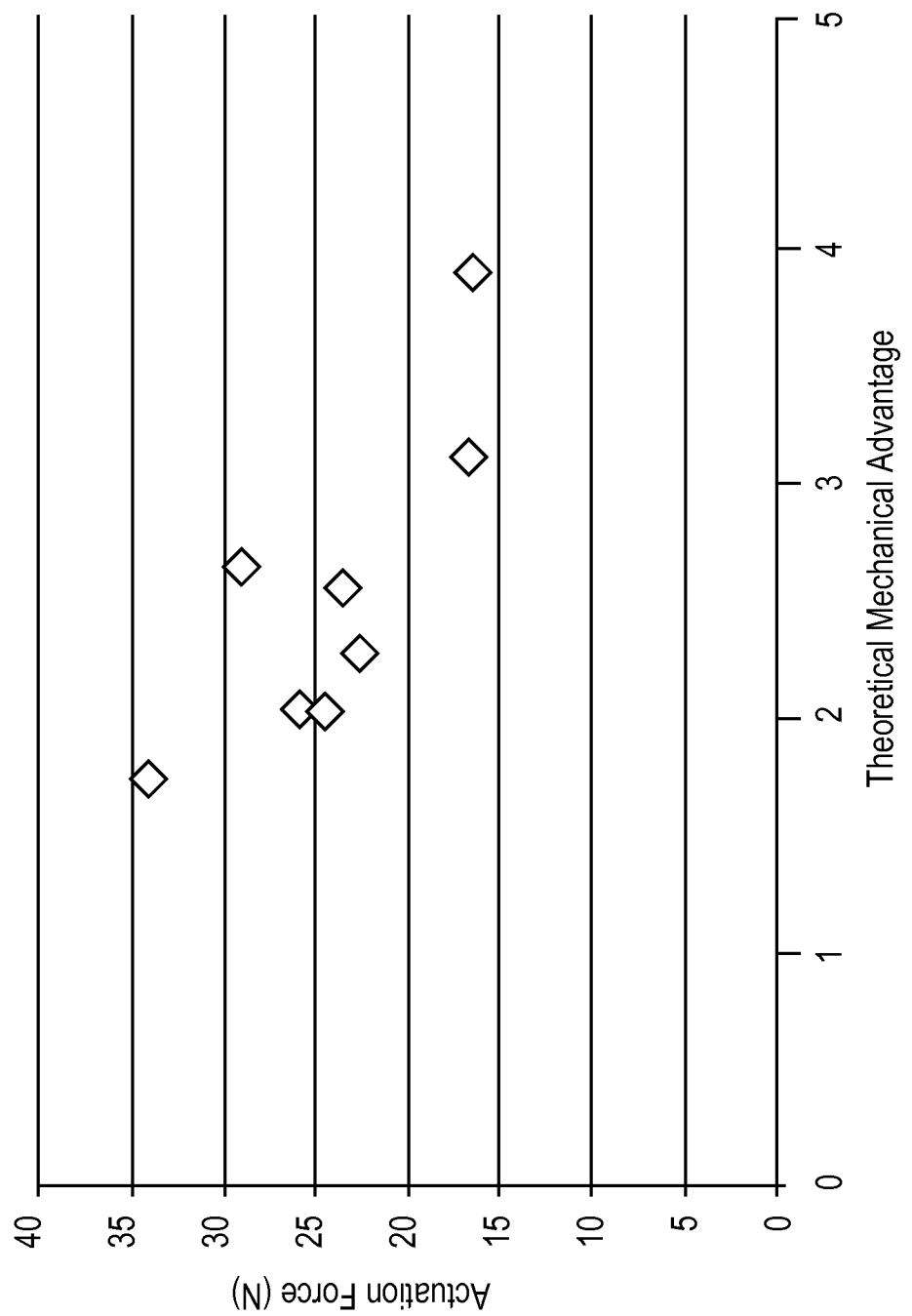
FIG. 8 is graph illustrating the relationship of the theoretical mechanical advantage to the actuation force required to dispel the contents of a dispenser having two pumps and dispensing a first and second composition.

FIG. 8 shows the relationship between the theoretical mechanical advantage and the actual force required to bring the depressible area 230 of a dispenser having two pumps pumping a first and second composition wherein first composition comprises a volatile solvent and the second composition comprises microcapsules to a final position; the final position being the state where the two pumps are no longer operative. In some examples, the dispenser 10 having two pumps may have a lever assembly 190 that provides a mechanical advantage of about 1 to about 5, preferably from about 1.5 to about 4, more preferably from about 2 to about 3. Thus, the introduction of a lever assembly significantly reduces the force that a user needs to apply to gain an acceptable spray pattern with a dual pump dispenser, ultimately ensuring that the user is able to achieve an adequate spray even when a customary amount of force is applied to the dual dispenser storing microcapsules and a volatile solvent separately.

It is to be understood that optional minor improvements such as valves to prevent reverse flow are to be included herein without deviating from the inventions herein. A non-limiting example is a valve included to prevent reverse flow from the swirl chamber to the channels. Other non-limiting minor improvements may include a mesh to prevent agglomerated particles from entering the pump.

Method of Use

The compositions disclosed herein may be applied to one or more skin surfaces and/or one or more mammalian keratinous tissue surfaces as part of a user's daily routine or regimen. Additionally or alternatively, the compositions herein may be used on an "as needed" basis. The composition may be applied to any article, such as a textile, or any absorbent article including, but not limited to, feminine hygiene articles, diapers, and adult incontinence articles. For example, while the combinations of the dispensers and compositions described herein are exquisitely designed to be used as a fine fragrance spray, it is understood that such combinations may also be used as a body spray, feminine spray, adult incontinence spray, baby spray, or other spray. The size, shape, and aesthetic design of the dispensers described herein may vary widely.

Compositions

Volatile Solvents

The compositions described herein may include a volatile solvent or a mixture of volatile solvents. The volatile solvents may comprise greater than 10%, greater than 30%, greater than 40%, greater than 50%, greater than 60%, greater than 70%, or greater than 90%, by weight of the composition. The volatile solvents useful herein may be relatively odorless and safe for use on human skin. Suitable volatile solvents may include $C_1$-$C_4$ alcohols and mixtures thereof. Some non-limiting examples of volatile solvents include ethanol, methanol, propanol, isopropanol, butanol, and mixtures thereof. In some examples, the composition may comprise from 0.01% to 98%, by weight of the composition, of ethanol or other volatile solvent(s).

Nonvolatile Solvents

The composition may comprise a nonvolatile solvent or a mixture of nonvolatile solvents. Non-limiting examples of nonvolatile solvents include benzyl benzoate, diethyl phthalate, isopropyl myristate, propylene glycol, dipropylene glycol, triethyl citrate, and mixtures thereof.

Fragrances

The composition may comprise a fragrance. As used herein, "fragrance" is used to indicate any odoriferous material or a combination of ingredients including at least one odoriferous material. Any fragrance that is cosmetically acceptable may be used in the composition. For example, the fragrance may be one that is a liquid or solid at room temperature. Generally, the non-encapsulated fragrance(s) may be present at a level from about 0.001% to about 40%, from about 0.1% to about 25%, from about 0.25% to about 20%, or from about 0.5% to about 15%, by weight of the composition. Some fragrances can be considered to be volatiles and other fragrances can be considered to be or non-volatiles, as described and defined herein.

A wide variety of chemicals are known as fragrances, non-limiting examples of which include alcohols, aldehydes, ketones, ethers, Schiff bases, nitriles, and esters. More commonly, naturally occurring plant and animal oils and exudates comprising complex mixtures of various chemical components are known for use as fragrances. Non-limiting examples of the fragrances useful herein include pro-fragrances such as acetal pro-fragrances, ketal pro-fragrances, ester pro-fragrances, hydrolyzable inorganic-organic pro-fragrances, and mixtures thereof. The fragrances may be released from the pro-fragrances in a number of ways. For example, the fragrance may be released as a result of simple hydrolysis, or by a shift in an equilibrium reaction, or by a pH-change, or by enzymatic release. The fragrances herein may be relatively simple in their chemical make-up, comprising a single chemical, or may comprise highly sophisticated complex mixtures of natural and synthetic chemical components, all chosen to provide any desired odor.

The fragrances may have a boiling point (BP) of about 500° C. or lower, about 400° C. or lower, or about 350° C. or lower. The BP of many fragrances are disclosed in *Perfume and Flavor Chemicals* (Aroma Chemicals), Steffen Arctander (1969). The C log P value of the individual fragrance materials may be about –0.5 or greater. As used herein, "C log P" means the logarithm to the base 10 of the octanol/water partition coefficient. The C log P can be readily calculated from a program called "C LOG P" which is available from Daylight Chemical Information Systems Inc., Irvine Calif., USA or calculated using Advanced Chemistry Development (ACD/Labs) Software V11.02 (© 1994-2014 ACD/Labs). Octanol/water partition coefficients are described in more detail in U.S. Pat. No. 5,578,563.

Examples of suitable aldehyde include but are not limited to: alpha-Amylcinnamaldehyde, Anisic Aldehyde, Decyl Aldehyde, Lauric aldehyde, Methyl n-Nonyl acetaldehyde, Methyl octyl acetaldehyde, Nonylaldehyde, Benzenecarboxaldehyde, Neral, Geranial, 2, 6 octadiene,1,1 diethoxy-3,7dimethyl-, 4-Isopropylbenzaldehyde, 2,4-Dimethyl-3-cyclohexene-1-carboxaldehyde, alpha-Methyl-p-isopropyldihydrocinnamaldehyde, 3-(3-isopropylphenyl) butanal, alpha-Hexylcinnamaldehyde, 7-Hydroxy-3,7-dimethyloctan-1-al, 2,4-Dimethyl-3-Cyclohexene-1-carboxaldehyde, Octyl Aldehyde, Phenylacetaldehyde, 2,4-Dimethyl-3-Cyclohexene-1-carboxaldehyde, Hexanal, 3,7-Dimethyloctanal, 6,6-Dimethylbicyclo[3.1.1]hept-2-ene-2-butanal, Nonanal, Octanal, 2-Nonenal Undecenal, 2-Methyl-4-(2,6,6-trimethyl-1-cyclohexenyl-1)-2-butenal, 2,6-Dimethyloctanal3-(p-Isopropylphenyl)propionaldehyde, 3-Phenyl-4-pentenal Citronellal, o/p-Ethyl-alpha,alpha-, 9-Decenal, dimethyldihydrocinnamaldehyde, p-Isobutyl-alpha-methylydrocinnamaldehyde, cis-4-Decen-1-al, 2,5-Dimethyl-2-ethenyl-4-hexenal, trans-2-Methyl-2-butenal, 3-Methylnonanal, alpha-Sinensal, 3-Phenylbutanal, 2,2-Dimethyl-3-phenylpropionaldehyde, m-tert.Butyl-alpha-methyldihydrocinnamic aldehyde, Geranyl oxyacetaldehyde, trans-4-Decen-1-al, Methoxycitronellal, and mixtures thereof.

Examples of suitable esters include but are not limited to: Allyl cyclohexanepropionate, Allyl heptanoate, Allyl Amyl Glycolate, Allyl caproate, Amyl acetate (n-Pentyl acetate), Amyl Propionate, Benzyl acetate, Benzyl propionate, Benzyl salicylate, cis-3-Hexenylacetate, Citronellyl acetate, Citronellyl propionate, Cyclohexyl salicylate, Dihydro Isojasmonate Dimethyl benzyl carbinyl acetate, Ethyl acetate, Ethyl acetoacetate, Ethyl Butyrate, Ethyl-2-methyl butyrate, Ethyl-2-methyl pentanoate Fenchyl acetate (1,3, 3-Trimethyl-2-norbornanyl acetate), Tricyclodecenyl acetate, Tricyclodecenyl propionate, Geranyl acetate, cis-3-Hexenyl isobutyrate, Hexyl acetate, cis-3-Hexenyl salicylate, n-Hexyl salicylate, Isobornyl acetate, Linalyl acetate, p-t-Butyl Cyclohexyl acetate, (–)-L-Menthyl acetate, o-t-Butylcyclohexyl acetate), Methyl benzoate, Methyl dihydro iso jasmonate, alpha-Methylbenzyl acetate, Methyl salicylate, 2-Phenylethyl acetate, Prenyl acetate, Cedryl acetate, Cyclabute, Phenethyl phenylacetate, Terpinyl formate, Citronellyl anthranilate, Ethyl tricyclo[5.2.1.0-2,6]decane-2-carboxylate, n-Hexyl ethyl acetoacetate, 2-tert.-Butyl-4-methyl-cyclohexyl acetate, Formic acid, 3,5,5-trimethylhexyl ester, Phenethyl crotonate, Cyclogeranyl acetate, Geranyl crotonate, Ethyl geranate, Geranyl isobutyrate, Ethyl 2-nonynoate2,6-Octadienoic acid, 3,7-dimethyl-, methyl ester, Citronellyl valerate, 2-Hexenylcyclopentanone, Cyclohexyl anthranilate, L-Citronellyl tiglate, Butyl tiglate, Pentyl tiglate, Geranyl caprylate, 9-Decenyl acetate,2-Isopropyl-5-methylhexyl-1 butyrate, n-Pentyl benzoate, 2-Methylbutyl benzoate (mixture with pentyl benzoate), Dimethyl benzyl carbinyl propionate, Dimethyl benzyl carbinyl acetate, trans-2-Hexenyl salicylate, Dimethyl benzyl carbinyl isobutyrate, 3,7-Dimethyloctyl formate, Rhodinyl formate, Rhodinyl isovalerate, Rhodinyl acetate, Rhodinyl butyrate, Rhodinyl propionate, Cyclohexylethyl acetate, Neryl butyrate, Tetrahydrogeranyl butyrate, Myrcenyl acetate, 2,5-Dimethyl-2-ethenylhex-4-enoic acid, methyl ester, 2,4-Dimethylcyclohexane-1-methyl acetate, Ocimenyl acetate, Linalyl isobutyrate, 6-Methyl-5-heptenyl-1 acetate, 4-Methyl-2-pentyl acetate, n-Pentyl 2-methylbutyrate, Propyl acetate, Isopropenyl acetate, Isopropyl acetate, 1-Methylcyclohex-3-enecarboxylic acid, methyl ester, Propyl tiglate, Propyl/isobutyl cyclopent-3-enyl-1-acetate (alpha-vinyl), Butyl 2-furoate, Ethyl 2-pentenoate, (E)-Methyl 3-pentenoate, 3-Methoxy-3-methylbutyl acetate, n-Pentyl crotonate, n-Pentyl isobutyrate, Propyl formate, Furfuryl butyrate, Methyl angelate, Methyl pivalate, Prenyl caproate, Furfuryl propionate, Diethyl malate, Isopropyl 2-methylbutyrate, Dimethyl malonate, Bornyl formate, Styralyl acetate, 1-(2-Furyl)-1-propanone, 1-Citronellyl acetate, 3,7-Dimethyl-1,6-nonadien-3-yl acetate, Neryl crotonate, Dihydromyrcenyl acetate, Tetrahydromyrcenyl acetate, Lavandulyl acetate, 4-Cyclooctenyl isobutyrate, Cyclopentyl isobutyrate, 3-Methyl-3-butenyl acetate, Allyl acetate, Geranyl formate, cis-3-Hexenyl caproate, and mixtures thereof.

Examples of suitable alcohols include but are not limited to: Benzyl alcohol, beta-gamma-Hexenol (2-Hexen-1-ol), Cedrol, Citronellol, Cinnamic alcohol, p-Cresol, Cumic alcohol, Dihydromyrcenol, 3,7-Dimethyl-1-octanol, Dimethyl benzyl carbinol, Eucalyptol, Eugenol, Fenchyl alcohol, Geraniol, Hydratopic alcohol, Isononyl alcohol (3,5,5-Trimethyl-1-hexanol), Linalool, Methyl Chavicol (Estragole), Methyl Eugenol (Eugenyl methyl ether), Nerol, 2-Octanol, Patchouli alcohol, Phenyl Hexanol (3-Methyl-5-phenyl-1-pentanol), Phenethyl alcohol, alpha-Terpineol, Tetrahydrolinalool, Tetrahydromyrcenol, 4-methyl-3decen-5-ol, 1-3,7-Dimethyloctane-1-ol, 2-(Furfuryl-2)-heptanol, 6,8-Dimethyl-2-nonanol, Ethyl norbornyl cyclohexanol, beta-Methyl cyclohexane ethanol, 3,7-Dimethyl-(2),6-octen (adien)-1-ol, trans-2-Undecen-1-ol 2-Ethyl-2-prenyl-3-hexenol, Isobutyl benzyl carbinol, Dimethyl benzyl carbinol, Ocimenol, 3,7-Dimethyl-1,6-nonadien-3-ol (cis & trans), Tetrahydromyrcenol, alpha-Terpineol, 9-Decenol-1,2 (Hexenyl)cyclopentanol, 2,6-Dimethyl-2-heptanol, 3-Methyl-1-octen-3-ol, 2,6-Dimethyl-5-hepten-2-ol, 3,7,9-Trimethyl-1,6-decadien-3-ol, 3,7-Dimethyl-6-nonen-1-ol, 3,7-Dimethyl-1-octyn-3-ol, 2,6-Dimethyl-1,5,7-octatrienol-3, Dihydromyrcenol, 2,6,10-Trimethyl-5,9-undecadienol, 2,5-Dimethyl-2-propylhex-4-enol-1,(Z),3-Hexenol, o,m,p-Methyl-phenylethanol, 2-Methyl-5-phenyl-1-pentanol, 3-Methylphenethyl alcohol, para-Methyl dimethyl benzyl carbinol, Methyl benzyl carbinol, p-Methylphenylethanol, 3,7-Dimethyl-2-octen-1-ol, 2-Methyl-6-methylene-7-octen-4-ol, and mixtures thereof.

Examples of ketones include but are not limited to: Oxacycloheptadec-10-en-2-one, Benzylacetone, Benzophenone, L-Carvone, cis-Jasmone, 4-(2,6,6-Trimethyl-3-cyclohexen-1-yl)-but-3-en-4-one, Ethyl amyl ketone, alpha-Ionone, Ionone Beta, Ethanone, Octahydro-2,3,8,8-tetramethyl-2-acetonaphthalene, alpha-Irone, 1-(5,5-Dimethyl-1-cyclohexen-1-yl)-4-penten-1-one, 3-Nonanone, Ethyl hexyl ketone, Menthone, 4-Methylacetophenone, gamma-Methyl Ionone Methyl pentyl ketone, Methyl Heptenone (6-Methyl-5-hepten-2-one), Methyl Heptyl ketone, Methyl Hexyl ketone, delta Muscenone, 2-Octanone, 2-Pentyl-3-methyl-2-cyclopenten-1-one, 2-Heptylcyclopentanone, alpha-Methylionone, 3-Methyl-2-(trans-2-pentenyl)-cyclopentenone, Octenyl cyclopentanone, n-Amylcyclopentenone, 6-Hydroxy-3,7-dimethyloctanoic acid lactone, 2-Hydroxy-2-cyclohexen-1-one, 3-Methyl-4-phenyl-3-buten-2-one, 2-Pentyl-2,5,5-trimethylcyclopentanone, 2-Cyclopentylcyclopentanol-1, 5-Methylhexan-2-one, gamma-Dodecalactone, delta-Dodecalactone delta-Dodecalactone, gamma-Nonalactone, delta-Nonalactone, gamma-Octalactone, delta-Undecalactone, gamma-Undecalactone, and mixtures thereof.

Examples of ethers include but are not limited to: p-Cresyl methyl ether, 4,6,6,7,8,8-Hexamethyl-1,3,4,6,7,8-hexahydro-cyclopenta(G)-2-benzopyran, beta-Naphthyl methyl ether, Methyl Iso Butenyl Tetrahydro Pyran, (Phantolide) 5-Acetyl-1,1,2,3,3,6 hexamethylindan, (Tonalid) 7-Acetyl-1,1,3,4,4,6-hexamethyltetralin, 2-Phenylethyl 3-methylbut-2-enyl ether, Ethyl geranyl ether, Phenylethyl isopropyl ether, and mixtures thereof.

Examples of alkenes include but are not limited to: Allo-Ocimene, Camphene, beta-Caryophyllene, Cadinene, Diphenylmethane, d-Limonene, Lymolene, beta-Myrcene, Para-Cymene, alpha-Pinene, beta-Pinene, alpha-Terpinene, gamma-Terpinene, Terpineolene, 7-Methyl-3-methylene-1,6-octadiene, and mixtures thereof.

Examples of nitriles include but are not limited to: 3,7-Dimethyl-6-octenenitrile, 3,7-Dimethyl-2(3), 6-nonadienenitrile, (2E,6Z) 2,6-nonadienenitrile, n-dodecane nitrile, and mixtures thereof.

Examples of Schiffs Bases include but are not limited to: Citronellyl nitrile, Nonanal/methyl anthranilate, Anthranilic acid, N-octylidene-, methyl ester(L)-, Hydroxycitronellal/methyl anthranilate, 2-Methyl-3-(4-Cyclamen aldehyde/methyl anthranilate, methoxyphenyl propanal/Methyl anthranilate, Ethyl p-aminobenzoate/hydroxycitronellal, Citral/methyl anthranilate, 2,4-Dimethylcyclohex-3-enecarbaldehyde methyl anthranilate, Hydroxycitronellal-indole, and mixtures thereof.

Non-limiting examples of fragrances include fragrances such as musk oil, civet, castoreum, ambergris, plant fragrances such as nutmeg extract, cardomon extract, ginger extract, cinnamon extract, patchouli oil, geranium oil, orange oil, mandarin oil, orange flower extract, cedarwood, vetyver, lavandin, ylang extract, tuberose extract, sandalwood oil, bergamot oil, rosemary oil, spearmint oil, peppermint oil, lemon oil, lavender oil, citronella oil, chamomille oil, clove oil, sage oil, neroli oil, labdanum oil, *eucalyptus* oil, *verbena* oil, *mimosa* extract, *narcissus* extract, carrot seed extract, jasmine extract, olibanum extract, rose extract, and mixtures thereof.

Carriers and Water

When the composition contains microcapsules, the composition may include a carrier for the microcapsules. Non-limiting examples of carriers include water, silicone oils like silicone D5, and other oils like mineral oil, isopropyl myristate, and fragrance oils. The carrier should b e one that does not significantly affect the performance of the microcapsules. Non-limiting examples of non-suitable carriers for the microcapsules include volatile solvents like 95% ethanol.

The compositions containing microcapsules may include about 0.1% to about 95%, from about 5% to about 95%, or from 5% to 75%, by weight of the composition, of the carrier. When the composition contains a volatile solvent, the composition may include from about 0.01% to about 40%, from about 0.1% to about 30%, or from about 0.1% to about 20%, by weight of the composition, of water.

In some examples, when a second composition containing a volatile solvent and a first composition containing microcapsules are sprayed, the dose containing the mixture of the first and second compositions may contain about 0.01% to about 75%, from about 1% to about 60%, from about 0.01% to about 60%, or from about 5% to about 50%, by weight of the composition, of water.

Encapsulates

The microcapsules may be any kind of microcapsule disclosed herein or known in the art. The microcapsules may be included from about 0.01% to about 45%, by weight, of the composition. The microcapsules may have a shell and a core material encapsulated by the shell. The core material of the microcapsules may include one or more fragrances or perfume oils. The shells of the microcapsules may be made from synthetic polymeric materials or naturally-occurring polymers. Synthetic polymers may be derived from petroleum oil, for example. Non-limiting examples of synthetic polymers include nylon, polyethylenes, polyamides, polystyrenes, polyisoprenes, polycarbonates, polyesters, polyureas, polyurethanes, polyolefins, polysaccharides, epoxy resins, vinyl polymers, polyacrylates, and mixtures thereof. Natural polymers occur in nature and may often be extracted from natural materials. Non-limiting examples of naturally occurring polymers are silk, wool, gelatin, cellulose, proteins, and combinations thereof.

The microcapsules may be friable microcapsules. A friable microcapsule is configured to release its core material when its shell is ruptured. The rupture may be caused by forces applied to the shell during mechanical interactions. The microcapsules may have a shell with a volume weighted fracture strength of from about 0.1 mega Pascals to about 15.0 mega Pascals, when measured according to the Fracture Strength Test Method described herein, or any incremental value expressed in 0.1 mega Pascals in this range, or any range formed by any of these values for fracture strength. As an example, a microcapsule may have a shell with a volume weighted fracture strength of 0.8-15.0 mega Pascals (MPa), alternatively from 5.0-12.0 mega Pascals (MPa), or alternatively from 6.0-10.0 mega Pascals (MPa).

The microcapsules may have a median volume-weighted particle size of from 2 microns to 80 microns, from 10 microns to 30 microns, or from 10 microns to 20 microns, as determined by the Test Method for Determining Median Volume-Weighted Particle Size of Microcapsules described herein.

The microcapsules may have various core material to shell weight ratios. The microcapsules may have a core material to shell ratio that is greater than or equal to: 70% to 30%, 75% to 25%, 80% to 20%, 85% to 15%, 90% to 10%, and 95% to 5%.

The microcapsules may have shells made from any material in any size, shape, and configuration known in the art. Some or all of the shells may include a polyacrylate material, such as a polyacrylate random copolymer. For example, the polyacrylate random copolymer may have a total polyacrylate mass, which includes ingredients selected from the group including: amine content of 0.2-2.0% of total polyacrylate mass; carboxylic acid of 0.6-6.0% of total polyacrylate mass; and a combination of amine content of 0.1-1.0% and carboxylic acid of 0.3-3.0% of total polyacrylate mass.

When a microcapsule's shell includes a polyacrylate material, and the shell has an overall mass, the polyacrylate material may form 5-100% of the overall mass, or any integer value for percentage in this range, or any range formed by any of these values for percentage. As examples, the polyacrylate material may form at least 5%, at least 10%, at least 25%, at least 33%, at least 50%, at least 70%, or at least 90% of the overall mass.

Some or all of the microcapsules may have various shell thicknesses. For at least a first group of the provided microcapsules, each microcapsule may have a shell with an overall thickness of 1-300 nanometers, or any integer value for nanometers in this range, or any range formed by any of these values for thickness. As an example, microcapsules may have a shell with an overall thickness of 2-200 nanometers.

The microcapsules may also encapsulate one or more benefit agents. The benefit agent(s) include, but are not limited to, cooling sensates, warming sensates, perfume oils, oils, pigments, dyes, chromogens, phase change materials, and other kinds of benefit agent known in the art, in any combination. In some examples, the perfume oil encapsulated may have a C log P of less than 4.5 or a C log P of less than 4. Alternatively the perfume oil encapsulated may have a C log P of less than 3. In some examples, the microcapsule may be anionic, cationic, zwitterionic, or have a neutral charge. The benefit agents(s) may be in the form of solids and/or liquids. The benefit agent(s) may be any kind of perfume oil(s) known in the art, in any combination.

The microcapsules may encapsulate a partitioning modifier in addition to the benefit agent. Non-limiting examples of partitioning modifiers include isopropyl myristate, mono-, di-, and tri-esters of $C_4$-$C_{24}$ fatty acids, castor oil, mineral oil, soybean oil, hexadecanoic acid, methyl ester isododecane, isoparaffin oil, polydimethylsiloxane, brominated vegetable oil, and combinations thereof. U.S. 2011-0268802 discloses other non-limiting examples of microcapsules and partitioning modifiers and is hereby incorporated by reference.

The microcapsule's shell may comprise a reaction product of a first mixture in the presence of a second mixture comprising an emulsifier, the first mixture comprising a reaction product of i) an oil soluble or dispersible amine with ii) a multifunctional acrylate or methacrylate monomer or oligomer, an oil soluble acid and an initiator, the emulsifier comprising a water soluble or water dispersible acrylic acid alkyl acid copolymer, an alkali or alkali salt, and optionally a water phase initiator. In some examples, said amine is an aminoalkyl acrylate or aminoalkyl methacrylate.

The microcapsules may include a core material and a shell surrounding the core material, wherein the shell comprises: a plurality of amine monomers selected from the group consisting of aminoalkyl acrylates, alkyl aminoalkyl acrylates, dialkyl aminoalykl acrylates, aminoalkyl methacrylates, alkylamino aminoalkyl methacrylates, dialkyl aminoalykl methacrylates, tertiarybutyl aminethyl methacrylates, diethylaminoethyl methacrylates, dimethylaminoethyl methacrylates, dipropylaminoethyl methacrylates, and mixtures thereof; and a plurality of multifunctional monomers or multifunctional oligomers. Non-limiting examples of emulsifiers include water-soluble salts of alkyl sulfates, alkyl ether sulfates, alkyl isothionates, alkyl carboxylates, alkyl sulfosuccinates, alkyl succinamates, alkyl sulfate salts such as sodium dodecyl sulfate, alkyl sarcosinates, alkyl derivatives of protein hydrolyzates, acyl aspartates, alkyl or alkyl ether or alkylaryl ether phosphate esters, sodium dodecyl sulphate, phospholipids or lecithin, or soaps, sodium, potassium or ammonium stearate, oleate or palmitate, alkylarylsulfonic acid salts such as sodium dodecylbenzenesulfonate, sodium dialkylsulfosuccinates, dioctyl sulfosuccinate, sodium dilaurylsulfosuccinate, poly(styrene sulfonate) sodium salt, isobutylene-maleic anhydride copolymer, gum arabic, sodium alginate, carboxymethylcellulose, cellulose sulfate and pectin, poly(styrene sulfonate), isobutylene-maleic anhydride copolymer, gum arabic, carrageenan, sodium alginate, pectic acid, tragacanth gum, almond gum and agar; semi-synthetic polymers such as carboxymethyl cellulose, sulfated cellulose, sulfated methylcellulose, carboxymethyl starch, phosphated starch, lignin sulfonic acid; and synthetic polymers such as maleic anhydride copolymers (including hydrolyzates thereof), polyacrylic acid, polymethacrylic acid, acrylic acid butyl acrylate copolymer or crotonic acid homopolymers and copolymers, vinylbenzenesulfonic acid or 2-acrylamido-2-methylpropanesulfonic acid homopolymers and copolymers, and partial amide or partial ester of such polymers and copolymers, carboxymodified polyvinyl alcohol, sulfonic acid-modified polyvinyl alcohol and phosphoric acid-modified polyvinyl alcohol, phosphated or sulfated tristyrylphenol ethoxylates, palmitamidopropyltrimonium chloride (Varisoft PATC™, available from Degussa Evonik, Essen, Germany), distearyl dimonium chloride, cetyltrimethylammonium chloride, quaternary ammonium compounds, fatty amines, aliphatic ammonium halides, alkyldimethylbenzylammonium halides, alkyldimethylethylammonium halides, polyethyleneimine, poly(2-dimethylamino)ethyl methacrylate) methyl chloride quaternary salt, poly(l-vinylpyrrolidone-co-2-dimethylaminoethyl methacrylate), poly(acrylamide-co-diallyldimethylammonium chloride), poly(allylamine), poly[bis(2-chloroethyl) ether-alt-1,3-bis[3-(dimethylamino)propyl]urea] quaternized, and poly(dimethylamine-co-epichlorohydrin-co-ethylenediamine), condensation products of aliphatic amines with alkylene oxide, quaternary ammonium compounds with a long-chain aliphatic radical, e.g. distearyldiammonium chloride, and fatty amines, alkyldimethylbenzylammonium halides, alkyldimethylethylammonium halides, polyalkylene glycol ether, condensation products of alkyl phenols, aliphatic alcohols, or fatty acids with alkylene oxide, ethoxylated alkyl phenols, ethoxylated arylphenols, ethoxylated polyaryl phenols, carboxylic esters solubilized with a polyol, polyvinyl alcohol, polyvinyl acetate, or copolymers of polyvinyl alcohol polyvinyl acetate, polyacrylamide, poly (N-isopropylacrylamide), poly(2-hydroxypropyl methacrylate), poly(-ethyl-2-oxazoline), poly(2-isopropenyl-2-oxazoline-co-methyl methacrylate), poly(methyl vinyl ether), and polyvinyl alcohol-co-ethylene), and cocoamidopropyl betaine.

Processes for making microcapsules are well known. Various processes for microencapsulation, and exemplary methods and materials, are set forth in U.S. Pat. No. 6,592,990; U.S. Pat. No. 2,730,456; U.S. Pat. No. 2,800,457; U.S. Pat. No. 2,800,458; U.S. Pat. No. 4,552,811; and U.S. 2006/0263518 A1.

The microcapsule may be spray-dried to form spray-dried microcapsules. The composition may also contain one or more additional delivery systems for providing one or more benefit agents, in addition to the microcapsules. The additional delivery system(s) may differ in kind from the microcapsules. For example, wherein the microcapsule encapsulates a perfume oil, the additional delivery system may be an additional fragrance delivery system, such as a moisture-triggered fragrance delivery system. Non-limiting examples of moisture-triggered fragrance delivery systems include cyclic oligosaccharide, starch (or other polysaccharide material), starch derivatives, and combinations thereof. Said polysaccharide material may or may not be modified.

The plurality of microcapsules may include anionic, cationic, and non-ionic microcapsules, in any combination, when included in a composition with a pH range of from 2 to about 10, alternatively from about 3 to about 9, alternatively from about 4 to about 8.

In some examples, the microcapsules may include a benefit agent comprising: a.) a perfume composition having a C log P of less than 4.5; b.) a perfume composition comprising, based on total perfume composition weight, 60% perfume materials having a C log P of less than 4.0; c.) a perfume composition comprising, based on total perfume composition weight, 35% perfume materials having a C log P of less than 3.5; d.) a perfume composition comprising, based on total perfume composition weight, 40% perfume materials having a C log P of less than 4.0 and at least 1% perfume materials having a C log P of less than 2.0; e.) a perfume composition comprising, based on total perfume composition weight, 40% perfume materials having a C log P of less than 4.0 and at least 15% perfume materials having a C log P of less than 3.0; f.) a perfume composition comprising, based on total perfume composition weight, at least 1% butanoate esters and at least 1% of pentanoate esters; g.) a perfume composition comprising, based on total perfume composition weight, at least 2% of an ester comprising an allyl moiety and at least 10% of another perfume comprising an ester moiety; h.) a perfume composition comprising, based on total perfume composition weight, at least 1% of an aldehyde comprising an alkyl chain moiety; i.) a perfume composition comprising, based on total perfume composition weight, at least 2% of a butanoate ester; j.) a perfume composition comprising, based on total perfume composition weight, at least 1% of a pentanoate ester; k.) a perfume composition comprising, based on total perfume composition weight, at least 3% of an ester comprising an allyl moiety and 1% of an aldehyde comprising an alkyl chain moiety; l.) a perfume composition comprising, based on total perfume composition weight, at least 25% of a perfume comprising an ester moiety and 1% of an aldehyde comprising an alkyl chain moiety; m.) a perfume compositions comprising, based on total perfume composition weight, at least 2% of a material selected from 4-(2,6,6-trimethyl-1-cyclohexenyl)-3-buten-2-one, 4-(2,6,6-trimethyl-2-cyclohexenyl)-3-buten-2-one and 3-buten-2-one,3-methyl-4-(2,6,6-trimehtyl-1-cyclohexen-2-yl)- and mixtures thereof; n.) a perfume composition comprising, based on total perfume composition weight, at least 0.1% of tridec-2-enonitrile, and mandaril, and mixtures thereof; o.) a perfume composition comprising, based on total perfume composition weight, at least 2% of a material selected from 3,7-dimethyl-6-octene nitrile, 2-cyclohexylidene-2-phenylacetonitrile and mixtures thereof; p.) a perfume composition comprising, based on total perfume composition weight, at least 80% of one or more perfumes comprising a moiety selected from the group consisting of esters, aldehydes, ionones, nitriles, ketones and combinations thereof; q.) a perfume composition comprising, based on total perfume composition weight, at least 3% of an ester comprising an allyl moiety; a perfume composition comprising, based on total perfume composition weight, at least 20% of a material selected from the group consisting of: 1-methylethyl-2-methylbutanoate; ethyl-2-methyl pentanoate; 1,5-dimethyl-1-ethenylhexyl-4-enyl acetate; p-metnh-1-en-8-yl acetate; 4-(2,6,6-trimethyl-2-cyclohexenyl)-3-buten-2-one; 4-acetoxy-3-methoxy-1-propenylbenzene; 2-propenyl cyclohexanepropionate; bicyclo[2.2.1]hept-5-ene-2-carboxylic acid,3-(1-methylethyl)-ethyl ester; bycyclo [2.2.1]heptan-2-ol, 1,7,7-trimethyl-, acetate; 1,5-dimethyl-1-ethenylhex-4-enylacetate; hexyl 2-methyl propanoate; ethyl-2-methylbutanoate; 4-undecanone; 5-heptyldihydro-2(3h)-furanone; 1,6-nonadien-3-ol,3,7dimethyl-; 3,7-dimethylocta-1,6-dien-3-o; 3-cyclohexene-1-carboxaldehyde,dimethyl-; 3,7-dimethyl-6-octene nitrile; 4-(2,6,6-trimethyl-1-cyclohexenyl)-3-buten-2-one; tridec-2-enonitrile; patchouli oil; ethyl tricycle [5.2.1.0]decan-2-carboxylate; 2,2-dimethyl-cyclohexanepropanol; hexyl ethanoate, 7-acetyl,1,2,3,4,5,6,7,8-octahydro-1,1,6,7-tetramethyl naphtalene; allyl-cyclohexyloxy acetate; methyl nonyl acetic aldehyde; 1-spiro[4,5]dec-7-en-7-yl-4-pentenen-1-one; 7-octen-2-ol,2-methyl-6-methylene-,dihydro; cyclohexanol,2-(1,1-dimethylethyl)-, acetate; hexahydro-4, 7-methanoinden-5(6)-yl propionatehexahydro-4,7-methanoinden-5(6)-yl propionate; 2-methoxynaphtalene; 1-(2,6,6-trimethyl-3-cyclohexenyl)-2-buten-1-one; 1-(2,6,6-trimethyl-2-cyclohexenyl)-2-buten-1-one; 3,7-dimethyloctan-3-ol; 3-buten-2-one,3-methyl-4-(2,6,6-trimehtyl-1-cyclohexen-2-yl)-; hexanoic acid, 2-propenyl ester; (z)-non-6-en-1-al; 1-decyl aldehyde; 1-octanal; 4-t-butyl-methylhydrocinnamaldehyde; alpha-hexylcinnamaldehyde; ethyl-2,4-hexadienoate; 2-propenyl 3-cyclohexanepropanoate; and mixtures thereof; r.) a perfume composition comprising, based on total perfume composition weight, at least 20% of a material selected from the group consisting of: 1-methylethyl-2-methylbutanoate; ethyl-2-methyl pentanoate; 1,5-dimethyl-1-ethenylhex-4-enyl acetate; p-menth-1-en-8-yl acetate; 4-(2,6,6-trimethyl-2-cyclohexenyl)-3-buten-2-one; 4-acetoxy-3-methoxy-1-propenylbenzene; 2-propenyl cyclohexanepropionate; bicyclo[2.2.1]hept-5-ene-2-carboxylic acid,3-(1-methylethyl)-ethyl ester; bycyclo [2.2.1]heptan-2-ol, 1,7,7-trimethyl-, acetate; 1,5-dimethyl-1-ethenylhex-4-enyl acetate; hexyl 2-methyl propanoate; ethyl-2-methylbutanoate,4-undecanolide; 5-heptyldihydro-2(3h)-furanone; 5-hydroxydodecanoic acid; decalactones; undecalactones, 1,6-nonadien-3-ol,3,7dimethyl-; 3,7-dimethylocta-1,6-dien-3-ol; 3-cyclohexene-1-carboxaldehyde,dimethyl-; 3,7-dimethyl-6-octene nitrile; 4-(2,6,6-trimethyl-1-cyclohexenyl)-3-buten-2-one; tridec-2-enonitrile; patchouli oil; ethyl tricycle [5.2.1.0]decan-2-carboxylate; 2,2-dimethyl-cyclohexanepropanol; allyl-cyclohexyloxy acetate; methyl nonyl acetic aldehyde; 1-spiro[4,5]dec-7-en-7-yl-4-pentenen-1-one; 7-octen-2-ol,2-methyl-6-methylene-,dihydro, cyclohexanol,2-(1,1-dimethylethyl)-, acetate; hexahydro-4,7-methanoinden-5(6)-yl propionatehexahydro-4,7-methanoinden-5(6)-yl propionate; 2-methoxynaphtalene; 1-(2,6,6-trimethyl-3-cyclohexenyl)-2-buten-1-one; 1-(2,6,6-trimethyl-2-cyclohexenyl)-2-buten-1-one; 3,7-dimethyloctan-3-ol; 3-buten-2-one,3-methyl-4-(2,6,6-trimehtyl-1-cyclohexen-2-yl)-; hexanoic acid, 2-propenyl ester; (z)-non-6-en-1-al; 1-decyl aldehyde; 1-octanal; 4-t-butyl-methylhydrocinnamaldehyde; ethyl-2,4-hexadienoate; 2-propenyl 3-cyclohexanepropanoate; and mixtures thereof; s.) a perfume composition comprising, based on total perfume composition weight, at least 5% of a material selected from the group consisting of 3-cyclohexene-1-carboxaldehyde,dimethyl-; 3-buten-2-one,3-methyl-4-(2,6,6-trimehtyl-1-cyclohexen-2-yl)-; patchouli oil; Hexanoic acid, 2-propenyl ester; 1-Octanal; 1-decyl aldehyde; (z)-non-6-en-1-al; methyl nonyl acetic aldehyde; ethyl-2-methylbutanoate; 1-methylethyl-2-methylbutanoate; ethyl-2-methyl pentanoate; 4-hydroxy-3-ethoxybenzaldehyde; 4-hydroxy-3-methoxybenzaldehyde; 3-hydroxy-2-methyl-4-pyrone; 3-hydroxy-2-ethyl-4-pyrone and mixtures thereof; t.) a perfume composition comprising, based on total perfume composition weight, less than 10% perfumes having a C log P greater than 5.0; u.) a perfume composition comprising geranyl palmitate; or v.) a perfume composition comprising a first and an optional second material, said first material having: (i) a C log P of at least 2; (ii) a boiling point of less than about 280° C.; and second optional second material, when present, having (i) a C log P of less than 2.5; and (ii) a ODT of less than about 100 ppb.

In some examples, the microcapsules may include a benefit agent comprising: one or more materials selected from the group consisting of (5-methyl-2-propan-2-ylcyclohexyl) acetate; 3,7-dimethyloct-6-en-1-al; 2-(phenoxy)ethyl 2-methylpropanoate; prop-2-enyl 2-(3-methylbutoxy)acetate; 3-methyl-1-isobutylbutyl acetate; prop-2-enyl hexanoate; prop-2-enyl 3-cyclohexylpropanoate; prop-2-enylheptanoate; (E)-1-(2,6,6-trimethyl-1-cyclohex-2-enyl)but-2-en-1-one; (E)-4-(2,6,6-trimethyl-2-cyclohexenyl)but-3-en-2-one; (E)-3-methyl-4-(2,6,6-trimethyl-1-cyclohex-2-enyl)but-3-en-2-one; 1-(2,6,6-trimethyl-1-cyclohex-2-enyl)pent-1-en-3-one; 6,6,9a-trimethyl-1,2,3a,4, 5,5a,7,8,9,9b-decahydronaphtho[2,1-b]furan; pentyl 2-hydroxybenzoate; 7,7-dimethyl-2-methylidene-norbornane; (E)-1-(2,6,6-trimethyl-1-cyclohexenyl)but-2-en-1-one; (E)-4-(2,6,6-trimethyl-1-cyclohexenyl)but-3-en-2-one; 4-ethoxy-4,8,8-trimethyl-9-methylidenebicyclo[3.3.1] nonane; (1,7,7-trimethyl-6-bicyclo[2.2.1]heptanyl) acetate; 3-(4-tert-butylphenyl)propanal; 1,1,2,3,3-pentamethyl-2,5,6,7-tetrahydroinden-4-one; 2-oxabicyclo2.2.2octane, 1methyl4(2,2,3trimethylcyclopentyl); [(Z)-hex-3-enyl] acetate; [(Z)-hex-3-enyl] 2-methylbutanoate; cis-3-hexenyl 2-hydroxybenzoate; 3,7-dimethylocta-2,6-dienal; 3,7-dimethyloct-6-en-1-al; 3,7-dimethyl-6-octen-1-ol; 3,7-dimethyloct-6-enyl acetate; 3,7-dimethyloct-6-enenitrile; 2-(3,7-dimethyloct-6-enoxy)acetaldehyde; tetrahydro-4-methyl-2-propyl-2h-pyran-4-yl acetate; ethyl 3-phenyloxirane-2-carboxylate; hexahydro-4,7-methano-indenyl isobutyrate; 2,4-dimethylcyclohex-3-ene-1-carbaldehyde; hexahydro-4,7-methano-indenyl propionate; 2-cyclohexylethyl acetate; 2-pentylcyclopentan-1-ol; (2R,3R,4S,5S,6R)-2-[(2R,3S,4R,5R,6R)-6-(6-cyclohexylhexoxy)-4,5-dihydroxy-2-(hydroxymethyl)oxan-3-yl]oxy-6-(hydroxymethyl)oxane-3,4,5-triol; (E)-1-(2,6,6-trimethyl-1-cyclohexa-1,3-dienyl)but-2-en-1-one; 1-cyclohexylethyl (E)-but-2-enoate; dodecanal; (E)-1-(2,6,6-trimethyl-1-cyclohex-3-enyl)but-2-en-1-one; (5E)-3-methylcyclopentadec-5-en-1-one; 4-(2,6,6-trimethyl-1-cyclohex-2-enyl)butan-2-one; 2-methoxy-4-propylphenol; methyl 2-hexyl-3-oxocyclopentane-1-carboxylate; 2,6-dimethyloct-7-en-2-ol; 4,7-dimethyloct-6-en-3-one; 4-(octahydro-4,7-methano-5H-inden-5-yliden)butanal; acetaldehyde ethyl linalyl acetal; ethyl 3,7-dimethyl-2,6-octadienoate; ethyl 2,6,6-trimethylcyclohexa-1,3-diene-1-carboxylate; 2-ethylhexanoate; (6E)-3,7-dimethylnona-1,6-dien-3-ol; ethyl 2-methylbutanoate; ethyl 2-methylpentanoate; ethyl tetradecanoate; ethyl nonanoate; ethyl 3-phenyloxirane-2-carboxylate; 1,4-dioxacycloheptadecane-5,17-dione; 1,3,3-trimethyl-2-oxabicyclo[2,2,2]octane; [essential oil]; oxacyclo-hexadecan-2-one; 3-(4-ethylphenyl)-2,2-dimethylpropanal; 2-butan-2-ylcyclohexan-1-one; 1,4-cyclohexandicarboxylic acid, diethyl ester; (3aalpha,4beta,7beta,7aalpha)-octahydro-4,7-methano-3aH-indene-3a-carboxylic acid ethyl ester; hexahydro-4-7, menthano-1H-inden-6-yl propionate; 2-butenon-1-one,1-(2,6-dimethyl-6-methylencyclohexyl)-; (E)-4-(2,2-dimethyl-6-methylidenecyclohexyl)but-3-en-2-one; 1-methyl-4-propan-2-ylcyclohexa-1,4-diene; 5-heptyloxolan-2-one; 3,7-dimethylocta-2,6-dien-1-ol; [(2E)-3,7-dimethylocta-2,6-dienyl] acetate; [(2E)-3,7-dimethylocta-2,6-dienyl] octanoate; ethyl 2-ethyl-6,6-dimethylcyclohex-2-ene-1-carboxylate; (4-methyl-1-propan-2-yl-1-cyclohex-2-enyl) acetate; 2-butyl-4,6-dimethyl-5,6-dihydro-2H-pyran; oxacyclohexadecen-2-one; 1-propanol,2-[1-(3,3-dimethyl-cyclohexyl)ethoxy]-2-methylpropanoate; 1-heptyl acetate; 1-hexyl acetate; hexyl 2-methylpropanoate; (2-(1-ethoxyethoxy)ethyl)benzene; 4,4a,5,9b-tetrahydroindeno[1,2-d][1,3]dioxine; undec-10-enal; 3-methyl-4-(2,6,6-trimethyl-2-cyclohexen-1-yl)-3-buten-2-one; 1-(1,2,3,4,5,6,7,8-octahydro-2,3,8,8-tetramethyl-2-naphthalenyl)-ethan-1-one; 7-acetyl,1,2,3,4,5,6,7-octahydro-1,1,6,7,-tetra methyl naphthalene; 3-methylbutyl 2-hydroxybenzoate; [(1R,4S,6R)-1,7,7-trimethyl-6-bicyclo[2.2.1]heptanyl] acetate; [(1R,4R,6R)-1,7,7-trimethyl-6-bicyclo[2.2.1]heptanyl] 2-methylpropanoate; (1,7,7-trimethyl-5-bicyclo[2.2.1]heptanyl) propanoate; 2-methylpropyl hexanoate; [2-methoxy-4-[(E)-prop-1-enyl]phenyl] acetate; 2-hexylcyclopent-2-en-1-one; 5-methyl-2-propan-2-ylcyclohexan-1-one; 7-methyloctyl acetate; propan-2-yl 2-methylbutanoate; 3,4,5,6,6-pentamethylheptenone-2; hexahydro-3,6-dimethyl-2(3H)-benzofuranone; 2,4,4,7-tetramethyl-6,8-nonadiene-3-one oxime; dodecyl acetate; [essential oil]; 3,7-dimethylnona-2,6-dienenitrile; [(Z)-hex-3-enyl] methyl carbonate; 2-methyl-3-(4-tert-butylphenyl)propanal; 3,7-dimethylocta-1,6-dien-3-ol; 3,7-dimethylocta-1,6-dien-3-yl acetate; 3,7-dimethylocta-1,6-dien-3-yl butanoate; 3,7-dimethylocta-1,6-dien-3-yl formate; 3,7-dimethylocta-1,6-dien-3-yl 2-methylpropanoate; 3,7-dimethylocta-1,6-dien-3-yl propanoate; 3-methyl-7-propan-2-ylbicyclo[2.2.2]oct-2-ene-5-carbaldehyde; 2,2-dimethyl-3-(3-methylphenyl)propan-1-ol; 3-(4-tert-butylphenyl)butanal; 2,6-dimethylhept-5-enal; 5-methyl-2-propan-2-yl-cyclohexan-1-ol; 1-(2,6,6-trimethyl-1-cyclohexenyl)pent-1-en-3-one; methyl 3-oxo-2-pentylcyclopentaneacetate; methyl tetradecanoate; 2-methylundecanal; 2-methyldecanal; 1,1-dimethoxy-2,2,5-trimethyl-4-hexene; [(1S)-3-(4-methylpent-3-enyl)-1-cyclohex-3-enyl]methyl acetate; 2-(2-(4-methyl-3-cyclohexen-1-yl)propyl)cyclo-pentanone; 4-penten-1-one, 1-(5,5-dimethyl-1-cyclohexen-1-yl; 1H-indene-ar-propanal,2,3,-dihydro-1,1-dimethyl-(9CI); 2-ethoxynaphthalene; nonanal; 2-(7,7-dimethyl-4-bicyclo[3.1.1]hept-3-enyl)ethyl acetate; octanal; 4-(1-methoxy-1-methylethyl)-1-methylcyclohexene; (2-tert-butylcyclohexyl) acetate; (E)-1-ethoxy-4-(2-methylbutan-2-yl)cyclohexane; 1,1-dimethoxynon-2-yne; [essential oil]; 2-cyclohexylidene-2-phenylacetonitrile; 2-cyclohexyl-1,6-heptadien-3-one; 4-cyclohexyl-2-methylbutan-2-ol; 2-phenylethyl 2-phenylacetate; (2E,5E/Z)-5,6,7-trimethyl octa-2,5-dien-4-one; 1-methyl-3-(4-methylpent-3-enyl)cyclohex-3-ene-1-carbaldehyde; methyl 2,2-dimethyl-6-methylidenecyclohexane-1-carboxylate; 1-(3,3-dimethylcyclohexyl)ethyl acetate; 4-methyl-2-(2-methylprop-1-enyl)oxane; 1-spiro(4.5)-7-decen-7-yl-4-penten-1-one; 4-(2-butenylidene)-3,5,5-trimethylcyclohex-2-en-1-one; 2-(4-methyl-1-cyclohex-3-enyl)propan-2-ol; 4-isopropylidene-1-methyl-cyclohexene; 2-(4-methyl-1-cyclohex-3-enyl)propan-2-yl acetate; 3,7-dimethyloctan-3-ol; 3,7-dimethyloctan-3-ol; 3,7-dimethyloctan-3-yl acetate; 3-phenylbutanal; (2,5-dimethyl-4-oxofuran-3-yl) acetate; 4-methyl-3-decen-5-ol; undec-10-enal; (4-formyl-2-methoxyphenyl) 2-methylpropanoate; 2,2,5-trimethyl-5-pentylcyclopentan-1-one; 2-tert-butylcyclohexan-1-ol; (2-tert-butylcyclohexyl) acetate; 4-tert-butylcyclohexyl acetate; 1-(3-methyl-7-propan-2-yl-6-bicyclo[2.2.2]oct-3-enyl)ethanone; (4,8-dimethyl-2-propan-2-ylidene-3,3a,4,5,6,8a-hexahydro-1H-azulen-6-yl) acetate; [(4Z)-1-cyclooct-4-enyl] methyl carbonate; methyl beta naphtyl ether; materials and stereoisomers thereof.

The compositions may also include a parent fragrance and one or more encapsulated fragrances that may or may not differ from the parent fragrance. For example, the composition may include a parent fragrance and a non-parent fragrance. A parent fragrance refers to a fragrance that is dispersed throughout the composition and is typically not encapsulated when added to the composition. Herein, a non-parent fragrance refers to a fragrance that differs from a parent fragrance included within the composition and is encapsulated with an encapsulating material prior to inclusion into the composition. Non-limiting examples of differences between a fragrance and a non-parent fragrance include differences in chemical make-up. In some examples, dried microcapsules may be incorporated into the composition, prepared by spray drying, fluid bed drying, tray drying, or other such drying processes that are available.

Suspending Agents

The compositions described herein may include one or more suspending agents to suspend the microcapsules and other water-insoluble material dispersed in the composition. The concentration of the suspending agent may range from about 0.01% to about 90%, alternatively from about 0.01% to 15% by weight of the composition.

Non-limiting examples of suspending agents include anionic polymers, cationic polymers, and nonionic polymers. Non-limiting examples of said polymers include vinyl polymers such as cross linked acrylic acid polymers with the CTFA name Carbomer, cellulose derivatives and modified cellulose polymers such as methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, polyvinyl alcohol, guar gum, hydroxypropyl guar gum, xanthan gum, arabia gum, tragacanth, galactan, carob gum, guar gum, karaya gum, carrageenan, pectin, agar, quince seed (*Cydonia oblonga* Mill), starch (rice, corn, potato, wheat), algae colloids (algae extract), microbiological polymers such as dextran, succinoglucan, pulleran, starch-based polymers such as carboxymethyl starch, methylhydroxypropyl starch, alginic acid-based polymers such as sodium alginate and alginic acid, propylene glycol esters, acrylate polymers such as sodium polyacrylate, polyethylacrylate, polyacrylamide, and polyethyleneimine, and inorganic water soluble material such as bentonite, aluminum magnesium silicate, laponite, hectonite, and anhydrous silicic acid. Other suspending agents may include, but are not limited to, Konjac, Gellan, and a methyl vinyl ether/maleic anhydride copolymer crosslinked with decadiene (e.g. Stabileze®).

Other non-limiting examples of suspending agents include cross-linked polyacrylate polymers like Carbomers with the trade names Carbopol® 934, Carbopol® 940, Carbopol® 950, Carbopol® 980, Carbopol® 981, Carbopol® Ultrez 10, Carbopol® Ultrez 20, Carbopol® Ultrez 21, Carbopol® Ultrez 30, Carbopol® ETD2020, Carbopol® ETD2050, Pemulen® TR-1, and Pemulen® TR-2, available from The Lubrizol Corporation; acrylates/steareth-20 methacrylate copolymer with trade name ACRYSOL™ 22 available from Rohm and Hass; acrylates/beheneth-25 methacrylate copolymers, trade names including Aculyn-28 available from Rohm and Hass, and Volarest™ FL available from Croda; nonoxynyl hydroxyethylcellulose with the trade name Amercell™ POLYMER HM-1500 available from Amerchol; methylcellulose with the trade name BENECEL®, hydroxyethyl cellulose with the trade name NATROSOL®; hydroxypropyl cellulose with the trade name KLUCEL®; cetyl hydroxyethyl cellulose with the trade name POLYSURF® 67, supplied by Hercules; ethylene oxide and/or propylene oxide based polymers with the trade names CARBOWAX® PEGs, POLYOX WASRs, and UCON® FLUIDS, all supplied by Amerchol; ammonium acryloyl dimethyltaurate/carboxyethyl-acrylate-crosspolymers like Aristoflex® TAC copolymer, ammonium acryloyl dimethyltaurate/VP copolymers like Aristoflex® AVS copolymer, sodium acryloyl dimethyltaurate/VP crosspolymers like Aristoflex® AVS copolymer, ammonium acryloyl dimethyltaurate/beheneth-25 methacrylate crosspolymers like Aristoflex® BVL or HMB, all available from Clariant Corporation; polyacrylate crosspoylmer-6 with the trade name Sepimax™ Zen, available from Seppic; and cross-linked copolymers of vinyl pyrrolidone and acrylic acid such as UltraThix™ P-100 polymer available from Ashland.

Other non-limiting examples of suspending agents include crystalline suspending agents which can be categorized as acyl derivatives, long chain amine oxides, and mixtures thereof.

Other non-limiting examples of suspending agents include ethylene glycol esters of fatty acids, in some aspects those having from about 16 to about 22 carbon atoms; ethylene glycol stearates, both mono and distearate, in some aspects, the distearate containing less than about 7% of the mono stearate; alkanol amides of fatty acids, having from about 16 to about 22 carbon atoms, or about 16 to 18 carbon atoms, examples of which include stearic monoethanolamide, stearic diethanolamide, stearic monoisopropanolamide and stearic monoethanolamide stearate; long chain acyl derivatives including long chain esters of long chain fatty acids (e.g., stearyl stearate, cetyl palmitate, etc.); long chain esters of long chain alkanol amides (e.g., stearamide diethanolamide distearate, stearamide monoethanolamide stearate); and glyceryl esters (e.g., glyceryl distearate, trihydroxystearin, tribehenin), a commercial example of which is Thixin® R available from Rheox, Inc. Other non-limiting examples of suspending agents include long chain acyl derivatives, ethylene glycol esters of long chain carboxylic acids, long chain amine oxides, and alkanol amides of long chain carboxylic acids.

Other non-limiting examples of suspending agents include long chain acyl derivatives including N,N-dihydrocarbyl amido benzoic acid and soluble salts thereof (e.g., Na, K), particularly N,N-di(hydrogenated) $C_{16}$, $C_{18}$ and tallow amido benzoic acid species of this family, which are commercially available from Stepan Company (Northfield, Ill., USA).

Non-limiting examples of suitable long chain amine oxides for use as suspending agents include alkyl dimethyl amine oxides (e.g., stearyl dimethyl amine oxide).

Other non-limiting suitable suspending agents include primary amines having a fatty alkyl moiety having at least about 16 carbon atoms, examples of which include palmitamine or stearamine, and secondary amines having two fatty alkyl moieties each having at least about 12 carbon atoms, examples of which include dipalmitoylamine or di(hydrogenated tallow)amine. Other non-limiting examples of suspending agents include di(hydrogenated tallow) phthalic acid amide, and cross-linked maleic anhydride-methyl vinyl ether copolymer.

Coloring Agents

The compositions herein may include a coloring agent. A coloring agent may be in the form of a pigment. As used herein, the term "pigment" means a solid that reflects light of certain wavelengths while absorbing light of other wavelengths, without providing appreciable luminescence. Useful pigments include, but are not limited to, those which are extended onto inert mineral(s) (e.g., talk, calcium carbonate, clay) or treated with silicone or other coatings (e.g., to prevent pigment particles from re-agglomerating or to change the polarity (hydrophobicity) of the pigment. Pigments may be used to impart opacity and color. Any pigment that is generally recognized as safe (such as those listed in C.T.F.A. cosmetic Ingredient Handbook, $3^{rd}$ Ed., cosmetic and Fragrance Association, Inc., Washington, D.C. (1982), herein incorporated by reference) may be included in the compositions described herein. Non-limiting examples of pigments include body pigment, inorganic white pigment, inorganic colored pigment, pearling agent, and the like. Non-limiting examples of pigments include talc, mica, magnesium carbonate, calcium carbonate, magnesium silicate, aluminum magnesium silicate, silica, titanium dioxide, zinc oxide, red iron oxide, yellow iron oxide, black iron oxide, ultramarine, polyethylene powder, methacrylate powder, polystyrene powder, silk powder, crystalline cellulose, starch, titanated mica, iron oxide titanated mica, bismuth oxychloride, and the like. The aforementioned pigments can be used independently or in combination.

Other non-limiting examples of pigments include inorganic powders such as gums, chalk, Fuller's earth, kaolin, sericite, muscovite, phlogopite, synthetic mica, lepidolite, biotite, lithia mica, vermiculite, aluminum silicate, starch, smectite clays, alkyl and/or trialkyl aryl ammonium smectites, chemically modified magnesium aluminum silicate, organically modified montmorillonite clay, hydrated aluminum silicate, fumed aluminum starch octenyl succinate barium silicate, calcium silicate, magnesium silicate, strontium silicate, metal tungstate, magnesium, silica alumina, zeolite, barium sulfate, calcined calcium sulfate (calcined gypsum), calcium phosphate, fluorine apatite, hydroxyapatite, ceramic powder, metallic soap (zinc stearate, magnesium stearate, zinc myristate, calcium palmitate, and aluminum stearate), colloidal silicone dioxide, and boron nitride; organic powder such as polyamide resin powder (nylon powder), cyclodextrin, methyl polymethacrylate powder, copolymer powder of styrene and acrylic acid, benzoguanamine resin powder, poly(ethylene tetrafluoride) powder, and carboxyvinyl polymer, cellulose powder such as hydroxyethyl cellulose and sodium carboxymethyl cellulose, ethylene glycol monostearate; inorganic white pigments such as magnesium oxide. Non-limiting examples of pigments include nanocolorants from BASF and multi-layer interference pigments such as Sicopearls from BASF. The pigments may be surface treated to provide added stability of color and ease of formulation. Non-limiting examples of pigments include aluminum, barium or calcium salts or lakes. Some other non-limiting examples of coloring agents include Red 3 Aluminum Lake, Red 21 Aluminum Lake, Red 27 Aluminum Lake, Red 28 Aluminum Lake, Red 33 Aluminum Lake, Yellow 5 Aluminum Lake, Yellow 6 Aluminum Lake, Yellow 10 Aluminum Lake, Orange 5 Aluminum Lake and Blue 1 Aluminum Lake, Red 6 Barium Lake, Red 7 Calcium Lake.

A coloring agent may also be a dye. Non-limiting examples include Red 6, Red 21, Brown, Russet and Sienna dyes, Yellow 5, Yellow 6, Red 33, Red 4, Blue 1, Violet 2, and mixtures thereof. Other non-limiting examples of dyes include fluorescent dyes like fluorescein.

Other Ingredients

The compositions may include other ingredients like antioxidants, ultraviolet inhibitors like sunscreen agents and physical sunblocks, cyclodextrins, quenchers, and/or skin care actives. Non-limiting examples of other ingredients include 2-ethylhexyl-p-methoxycinnamate; hexyl 2-[4-(diethylamino)-2-hydroxybenzoyl]benzoate; 4-tert-butyl-4'-methoxy dibenzoylmethane; 2-hydroxy-4-methoxybenzophenone; 2-phenylbenzimidazole-5-sulfonic acid; octocrylene; zinc oxide; titanium dioxide; vitamins like vitamin C, vitamin B, vitamin A, vitamin E, and derivatives thereof; flavones and flavonoids; amino acids like glycine, tyrosine, etc.; carotenoids and carotenes; chelating agents like EDTA, lactates, citrates, and derivatives thereof.

First and Second Compositions

The dispenser may include a first composition stored in a first reservoir and a second composition stored in the second reservoir. The second composition may include a volatile solvent and a first fragrance. The first composition may include a plurality of microcapsules and a carrier such as water. The first composition my further include a suspending agent. The first and second compositions may each further include any other ingredient listed herein unless such an ingredient negatively affects the performance of the microcapsules. Non-limiting examples of other ingredients include a coloring agent included in at least one of the first and second compositions and at least one non-encapsulated fragrance in the first composition or second composition.

When the first comprises microcapsules encapsulating a fragrance, the first compositions may further include a non-encapsulated fragrance that may or may not differ from the encapsulated fragrance in chemical make-up. In some examples, the first composition may be substantially free of a material selected from the group consisting of a propellant, a volatile solvent like ethanol, a detersive surfactant, and combinations thereof; preferably free of a material selected from the group consisting of a propellant, a volatile solvent like ethanol, a detersive surfactant, and combinations thereof. Non-limiting examples of propellants include compressed air, nitrogen, inert gases, carbon dioxide, gaseous hydrocarbons like propane, n-butane, isobutene, cyclopropane, and mixtures thereof. In some examples, the second composition may be substantially free of a material selected from the group consisting of a propellant, microcapsules, a detersive surfactant, and combinations thereof; preferably free of a material selected from the group consisting of propellant, microcapsules, a detersive surfactant, and combinations thereof. At least some of the microcapsules included in such a dispenser may encapsulate a fragrance. The fragrance encapsulated within the microcapsules may or may not differ in chemical make-up from the non-encapsulated fragrance included with the volatile solvent.

In some examples, the first composition may include at least 50%, at least 75%, or even at least 90%, by weight of the composition, of water; a plurality of microcapsules; and from about 0.01% to about 90%, preferably from about 0.01% to about 15%, more preferably from about 0.5% to about 15%, by weight of the composition, of a suspending agent; wherein the composition is free of propellants, volatile solvents (e.g. ethanol), and detersive surfactants; wherein the microcapsules comprise a first fragrance and a shell that surrounds said first fragrance. In some examples, the first composition may be substantially free of, or alternatively, free of a wax, an antiperspirant, and combinations thereof. In some examples, the first composition may comprise about 20% or less, about 10% or less, about 7% or less, of the microcapsules. It is to be appreciated that because the first composition is to be atomized, the concentration of the microcapsules in the first composition should not be so high as to prevent suitable atomization.

Test Methods

It is understood that the test methods that are disclosed in the Test Methods Section of the present application should be used to determine the respective values of the parameters of Applicants' invention as such invention is described and claimed herein.

(1) Fracture Strength a.) Place 1 gram of particles in 1 liter of distilled deionized (DI) water.
b.) Permit the particles to remain in the DI water for 10 minutes and then recover the particles by filtration.
c.) Determine the average rupture force of the particles by averaging the rupture force of 50 individual particles. The rupture force of a particle is determined using the procedure given in Zhang, Z.; Sun, G; "Mechanical Properties of Melamine-Formaldehyde microcapsules," J. Microencapsulation, vol 18, no. 5, pages 593-602, 2001. Then calculate the average fracture strength by dividing the average rupture force (in Newtons) by the average cross-sectional area of the spherical particle ($\pi r^2$, where r is the radius of the particle before compression), said average cross-sectional area being determined as follows:

(i) Place 1 gram of particles in 1 liter of distilled deionized (DI) water.
(ii) Permit the particles to remain in the DI water for 10 minutes and then recover the particles by filtration.
(iii) Determine the particle size distribution of the particle sample by measuring the particle size of 50 individual particles using the experimental apparatus and method of Zhang, Z.; Sun, G; "Mechanical Properties of MelamineFormaldehyde microcapsules," J. Microencapsulation, vol 18, no. 5, pages 593-602, 2001.
(iv) Average the 50 independent particle diameter measurements to obtain an o average particle diameter.

d.) For a capsule slurry, the sample is divided into three particle size fractions covering the particle size distribution. Per particle size fraction about 30 fracture strengths are determined.

(2) C log P

The "calculated log P" (C log P) is determined by the fragment approach of Hansch and Leo (cf., A. Leo, in Comprehensive Medicinal Chemistry, Vol. 4, C. Hansch, P. G. Sammens, J. B. Taylor, and c. A. Ramsden, Eds. P. 295, Pergamon Press, 1990, incorporated herein by reference). C log P values may be calculated by using the "C LOG P" program available from Daylight Chemical Information Systems Inc. of Irvine, Calif. U.S.A.

(3) Boiling Point

Boiling point is measured by ASTM method D2887-04a, "Standard Test Method for Boiling Range Distribution of Petroleum Fractions by Gas Chromatography," ASTM International.

(4) Volume Weight Fractions

Volume weight fractions are determined via the method of single-particle optical sensing (SPOS), also called optical particle counting (OPC). Volume weight fractions are determined via an Accusizer 780/AD supplied by Particle Sizing Systems of Santa Barbara Calif., U.S.A. or equivalent.

Procedure:

1) Put the sensor in a cold state by flushing water through the sensor;
2) Confirm background counts are less than 100 (if more than 100, continue the flush)
3) Prepare particle standard: pipette approx. 1 ml of shaken particles into a blender filled with approx. 2 cups of DI water. Blend it. Pipette approx. 1 ml of diluted, blended particles into 50 ml of DI water.
4) Measure particle standard: pipette approx. 1 ml of double diluted standard into Accusizer bulb. Press the start measurement-Autodilution button. Confirm particles counts are more than 9200 by looking in the status bar. If counts are less than 9200, press stop and 10 inject more sample.
5) Immediately after measurement, inject one full pipette of soap (5% Micro 90) into bulb and press the Start Automatic Flush Cycles button.

(5) Volume Weighted Fracture Strength (VWFS)

$$VWFS = (\text{fracture strength}_1 \times \text{volume fraction}_1) + (\text{fracture strength}_2 \times \text{volume fraction}_2) + (\text{fracture strength}_3 \times \text{volume fraction}_3)$$

Fracture strength$_1$=average fracture strength measured from a pool of 10 microcapsules (with similar particle size)

Volume fraction$_1$=volume fraction determined via Accusizer of particle distribution corresponding to fracture strength$_1$ The spread around the fracture strength to determine the volume fraction is determined as follows:

For particle batches with a mean particle sizes of about 15 micrometers a spread of about 10 micrometers is used, for particle batches with a mean particle sizes of about 30 micrometers and above, a spread of about 10 to 15 micrometers is used.

| Particle Batch | Mean Particle Size | Fracture Strength Determination at 3 particle sizes | Volume Fractions | Volume Fracture Strength |
|---|---|---|---|---|
| Melamine-based polyurea | 31 microns | 21 micron, 1.8 MPa; 31 micron, 1.6 MPa; 41 micron, 1.2 MPa) | 1 to 25 microns, 30%; 25 to 36 microns, 40%; 36 to 50 microns, 30% | 1.5 MPa |

(6) Benefit Agent Leakage Test
a.) Obtain 2, one gram samples of benefit agent particle composition.
b.) Add 1 gram (Sample 1) of particle composition to 99 grams of product matrix that the particle will be employed in and with the second sample immediately proceed to Step d below.
c.) Age the particle containing product matrix (Sample 1) of a.) above for 2 weeks at 35° C. in a sealed, glass jar.
d.) Recover the particle composition's particles from the product matrix of c.) (Sample 1 in product matrix) and from particle composition (Sample 2) above by filtration.
e.) Treat each particle sample from d.) above with a solvent that will extract all the benefit agent from each samples' particles.
f.) Inject the benefit agent containing solvent from each sample from e.) above into a Gas Chromatograph and integrate the peak areas to determine the total quantity of benefit agent extracted from each sample.
g.) The benefit agent leakage is defined as:
Value from f.) above for Sample 2—Value from f.) above for Sample 1.

(7) Test Method for Determining Median Volume-Weighted Particle Size of Microcapsules One skilled in the art will recognize that various protocols may be constructed for the extraction and isolation of microcapsules from finished products, and will recognize that such methods require validation via a comparison of the resulting measured values, as measured before and after the microcapsules' addition to and extraction from the finished product. The isolated microcapsules are then formulated in deionized water to form a capsule slurry for characterization for particle size distribution.

The median volume-weighted particle size of the microcapsules is measured using an Accusizer 780A, made by Particle Sizing Systems, Santa Barbara Calif., or equivalent. The instrument is calibrated from 0 to 300 µm using particle size standards (as available from Duke/Thermo-Fisher-Scientific Inc., Waltham, Mass., USA). Samples for particle size evaluation are prepared by diluting about 1 g of capsule slurry in about 5 g of de-ionized water and further diluting about 1 g of this solution in about 25 g of water. About 1 g of the most dilute sample is added to the Accusizer and the testing initiated using the autodilution feature. The Accusizer should be reading in excess of 9200 counts/second. If the counts are less than 9200 additional sample should be added. Dilute the test sample until 9200 counts/second and then the evaluation should be initiated. After 2 minutes of testing the Accusizer will display the results, including the median volume-weighted particle size.

EXAMPLES

The following examples are given solely for the purpose of illustration and are not to be construed as limiting the invention, as many variations thereof are possible.

In the examples, all concentrations are listed as weight percent, unless otherwise specified and may exclude minor materials such as diluents, filler, and so forth. The listed formulations, therefore, comprise the listed components and any minor materials associated with such components. As is apparent to one of ordinary skill in the art, the selection of these minor materials will vary depending on the physical and chemical characteristics of the particular ingredients selected to make the present invention as described herein.

Example 1

Polyacrylate Microcapsule

An oil solution, consisting of 128.4 g Fragrance Oil, 32.1 g isopropyl myristate, 0.86 g DuPont Vazo-67, 0.69 g Wako Chemicals V-501, is added to a 35° C. temperature controlled steel jacketed reactor, with mixing at 1000 rpm (4 tip, 2" diameter, flat mill blade) and a nitrogen blanket applied at 100 cc/min. The oil solution is heated to 70° C. in 45 minutes, held at 75° C. for 45 minutes, and cooled to 50° C. in 75 minutes. This will be called oil solution A.

In a reactor vessel, an aqueous solution is prepared consisting of 300 g deionized water to which is dispersed 2.40 grams of Celvol 540 polyvinyl alcohol at 25 degrees Centigrade. The mixture is heated to 85 degrees Centigrade and held there for 45 minutes. The solution is cooled to 30 degrees Centigrade. 1.03 grams of Wako Chemicals V-501 initiator is added, along with 0.51 grams of 40% sodium hydroxide solution. Heat the solution to 50° C., and maintain the solution at that temperature.

To the oil solution A, add 0.19 grams of tert-butyl amino ethyl methacrylate (Sigma Aldrich), 0.19 grams of beta-carboxy ethyl acrylate (Sigma Aldrich), and 15.41 grams of Sartomer CN975 (Sartomer, Inc.). Mix the acrylate monomers into the oil phase for 10 minutes. This will be called oil solution B. Use a Caframo mixer with a 4-blade pitched turbine agitator.

Start nitrogen blanket on top of the aqueous solution in reactor. Start transferring the oil solution B into the aqueous solution in the reactor, with minimal mixing. Increase mixing to 1800-2500 rpm, for 60 minutes to emulsify the oil phase into the water solution. After milling is completed, mixing is continued with a 3" propeller at 350 rpm. The batch is held at 50° C. for 45 minutes, the temperature is increased to 75° C. in 30 minutes, held at 75° C. for 4 hours, heated to 95° C. in 30 minutes and held at 95° C. for 6 hours. The batch is then allowed to cool to room temperature. The resultant microcapsules have a median particle size of 12.6 microns, a fracture strength of 7.68±2.0 MPa, and a 51%±20% deformation at fracture.

Example 2

Polyacrylate Microcapsules

An oil solution, consisting of 96 g Fragrance Oil, 64 g isopropyl myristate, 0.86 g DuPont Vazo-67, 0.69 g Wako Chemicals V-501, is added to a 35° C. temperature controlled steel jacketed reactor, with mixing at 1000 rpm (4 tip, 2" diameter, flat mill blade) and a nitrogen blanket applied at 100 cc/min. The oil solution is heated to 70° C. in 45 minutes, held at 75° C. for 45 minutes, and cooled to 50° C. in 75 minutes. This will be called oil solution A.

In a reactor vessel, an aqueous solution is prepared consisting of 300 g deionized water to which is dispersed 2.40 grams of Celvol 540 polyvinyl alcohol at 25 degrees Centigrade. The mixture is heated to 85 degrees Centigrade and held there for 45 minutes. The solution is cooled to 30 degrees Centigrade. 1.03 grams of Wako Chemicals V-501 initiator is added, along with 0.51 grams of 40% sodium hydroxide solution. Heat the solution to 50° C., and maintain the solution at that temperature.

To the oil solution A, add 0.19 grams of tert-butyl amino ethyl methacrylate (Sigma Aldrich), 0.19 grams of beta-carboxy ethyl acrylate (Sigma Aldrich), and 15.41 grams of Sartomer CN975 (Sartomer, Inc.). Mix the acrylate monomers into the oil phase for 10 minutes. This will be called oil solution B. Use a Caframo mixer with a 4-blade pitched turbine agitator.

Start nitrogen blanket on top of the aqueous solution in reactor. Start transferring the oil solution B into the aqueous solution in the reactor, with minimal mixing. Increase mixing to 1800-2500 rpm, for 60 minutes to emulsify the oil phase into the water solution. After milling is completed, mixing is continued with a 3" propeller at 350 rpm. The batch is held at 50° C. for 45 minutes, the temperature is increased to 75° C. in 30 minutes, held at 75° C. for 4 hours, heated to 95° C. in 30 minutes and held at 95° C. for 6 hours. The batch is then allowed to cool to room temperature.

The resultant microcapsules have a median particle size of 12.6 microns, a fracture strength of 2.60±1.2 MPa, 37%±15% deformation at fracture.

Example 3

Polyacrylate Microcapsules

An oil solution, consisting of 128.4 g Fragrance Oil, 32.1 g isopropyl myristate, 0.86 g DuPont Vazo-67, 0.69 g Wako Chemicals V-501, is added to a 35° C. temperature controlled steel jacketed reactor, with mixing at 1000 rpm (4 tip, 2" diameter, flat mill blade) and a nitrogen blanket applied at 100 cc/min. The oil solution is heated to 70° C. in 45 minutes, held at 75° C. for 45 minutes, and cooled to 50° C. in 75 minutes. This will be called oil solution A.

In a reactor vessel, an aqueous solution is prepared consisting of 300 g deionized water to which is dispersed 2.40 grams of Celvol 540 polyvinyl alcohol at 25 degrees Centigrade. The mixture is heated to 85 degrees Centigrade and held there for 45 minutes. The solution is cooled to 30 degrees Centigrade. 1.03 grams of Wako Chemicals V-501 initiator is added, along with 0.51 grams of 40% sodium hydroxide solution. Heat the solution to 50° C., and maintain the solution at that temperature.

To the oil solution A, add 0.19 grams of tert-butyl amino ethyl methacrylate (Sigma Aldrich), 0.19 grams of beta-carboxy ethyl acrylate (Sigma Aldrich), and 15.41 grams of Sartomer CN975 (Sartomer, Inc.). Mix the acrylate monomers into the oil phase for 10 minutes. This will be called oil solution B. Use a Caframo mixer with a 4-blade pitched turbine agitator.

Start nitrogen blanket on top of the aqueous solution in reactor. Start transferring the oil solution B into the aqueous solution in the reactor, with minimal mixing. Increase mixing to 1300-1600 rpm, for 60 minutes to emulsify the oil phase into the water solution. After milling is completed, mixing is continued with a 3" propeller at 350 rpm. The batch is held at 50° C. for 45 minutes, the temperature is increased to 75° C. in 30 minutes, held at 75° C. for 4 hours, heated to 95° C. in 30 minutes and held at 95° C. for 6 hours. The batch is then allowed to cool to room temperature.

The resultant microcapsules have a median particle size of 26.1 microns, a fracture strength of 1.94±1.2 MPa, 30%±14% deformation at fracture.

Example 4

Polyacrylate Microcapsules

An oil solution, consisting of 128.4 g Fragrance Oil, 32.1 g isopropyl myristate, 0.86 g DuPont Vazo-67, 0.69 g Wako Chemicals V-501, is added to a 35° C. temperature controlled steel jacketed reactor, with mixing at 1000 rpm (4 tip, 2" diameter, flat mill blade) and a nitrogen blanket applied at 100 cc/min. The oil solution is heated to 70° C. in 45 minutes, held at 75° C. for 45 minutes, and cooled to 50° C. in 75 minutes. This will be called oil solution A.

In a reactor vessel, an aqueous solution is prepared consisting of 300 g deionized water to which is dispersed 2.40 grams of Celvol 540 polyvinyl alcohol at 25 degrees Centigrade. The mixture is heated to 85 degrees Centigrade and held there for 45 minutes. The solution is cooled to 30 degrees Centigrade. 1.03 grams of Wako Chemicals V-501 initiator is added, along with 0.51 grams of 40% sodium hydroxide solution. Heat the solution to 50° C., and maintain the solution at that temperature.

To the oil solution A, add 0.19 grams of tert-butyl amino ethyl methacrylate (Sigma Aldrich), 0.19 grams of beta-carboxy ethyl acrylate (Sigma Aldrich), and 15.41 grams of Sartomer CN975 (Sartomer, Inc.). Mix the acrylate monomers into the oil phase for 10 minutes. This will be called oil solution B. Use a Caframo mixer with a 4-blade pitched turbine agitator.

Start nitrogen blanket on top of the aqueous solution in reactor. Start transferring the oil solution B into the aqueous solution in the reactor, with minimal mixing. Increase mixing to 2500-2800 rpm, for 60 minutes to emulsify the oil phase into the water solution. After milling is completed, mixing is continued with a 3" propeller at 350 rpm. The batch is held at 50° C. for 45 minutes, the temperature is increased to 75° C. in 30 minutes, held at 75° C. for 4 hours, heated to 95° C. in 30 minutes and held at 95° C. for 6 hours. The batch is then allowed to cool to room temperature.

The resultant microcapsules have a median particle size of 10.0 microns, a fracture strength of 7.64±2.2 MPa, 56%±20% deformation at fracture.

Example 5

Polyurea/Urethane Microcapsules

An aqueous solution, consisting of 6.06 g Celvol 523 polyvinyl alcohol (Celanese Chemicals) and 193.94 g deionized water, is added into a temperature controlled steel jacketed reactor at room temperature. Then an oil solution, consisting of 75 g Scent A and 25 g Desmodur N3400 (polymeric hexamethylene diisocyanate), is added into the reactor. The mixture is emulsified with a propeller (4 tip, 2" diameter, flat mill blade; 2200 rpm) to desired emulsion droplet size. The resulting emulsion is then mixed with a Z-bar propeller at 450 rpm. An aqueous solution, consisting of 47 g water and 2.68 g tetraethylenepentamine, is added into the emulsion. And it is then heated to 60° C., held at 60° C. for 8 hours, and allowed to cool to room temperature. The median particle size of the resultant microcapsules is 10 microns.

Example 6

Polyurea/Urethane Microcapsules

Prepare the Oil Phase by adding 4.44 grams of isophorone diisocyanate (Sigma Aldrich) to 5.69 grams of Scent A fragrance oil. Prepare a Water Phase by mixing 1.67 grams of Ethylene Diamine (Sigma Aldrich) and 0.04 grams of 1,4-Diazabicyclo[2.2.2]octane (Sigma Aldrich) into 40 grams of a 5 wt % aqueous solution of Polyvinylpyrrolidone K-90 (Sigma Aldrich) at 10 degrees Centigrade. Next, add the Oil Phase contents to 15.0 grams of a 5 wt % aqueous solution of Polyvinylpyrrolidone K-90 (Sigma Aldrich), while agitating the mix at 1400 RPM using a Janke & Kunkel IKA Laboretechnik RW20 DZM motor with a 3-blade turbine agitator for approximately 9 minutes. Next, add the addition of the Water Phase into the emulsified Oil Phase dropwise over a 6.5 minute period, while continuing to agitate at 1400 RPM. Continue to agitate for 23 minutes, then reduce the agitation speed to 1000 RPM. After 3.75 additional hours, reduce the agitation speed to 500 RPM, and continue to agitate for 14 hours. Start heating the dispersion to 50 degrees Centigrade, over a 2 hour period. Age the capsules at 50 C for 2 hours, then collect the microcapsules. The resultant microcapsules have a median particle size of 12 microns.

Example 7

Polyacrylate Microcapsules

The polyacrylate microcapsule with the characteristics displayed in Table 3 may be prepared as follows. An oil solution, consisting of 112.34 g Fragrance Oil, 12.46 g isopropyl myristate, 2.57 g DuPont Vazo-67, 2.06 g Wako Chemicals V-501, is added to a 35° C. temperature controlled steel jacketed reactor, with mixing at 1000 rpm (4 tip, 2" diameter, flat mill blade) and a nitrogen blanket applied at 100 cc/min. The oil solution is heated to 70° C. in 45 minutes, held at 75° C. for 45 minutes, and cooled to 50° C. in 75 minutes. This will be called oil solution A.

In a reactor vessel, an aqueous solution is prepared consisting of 300 g deionized water to which is dispersed 2.40 grams of Celvol 540 polyvinyl alcohol at 25 degrees Centigrade. The mixture is heated to 85 degrees Centigrade and held there for 45 minutes. The solution is cooled to 30 degrees Centigrade. 1.03 grams of Wako Chemicals V-501 initiator is added, along with 0.51 grams of 40% sodium hydroxide solution. Heat the solution to 50° C., and maintain the solution at that temperature.

To the oil solution A, add 0.56 grams of tert-butyl amino ethyl methacrylate (Sigma Aldrich), 0.56 grams of beta-carboxy ethyl acrylate (Sigma Aldrich), and 46.23 grams of Sartomer CN975 (Sartomer, Inc.). Mix the acrylate monomers into the oil phase for 10 minutes. This will be called oil solution B. Use a Caframo mixer with a 4-blade pitched turbine agitator.

Start nitrogen blanket on top of the aqueous solution in reactor. Start transferring the oil solution B into the aqueous solution in the reactor, with minimal mixing. Increase mixing to 1800-2500 rpm, for 60 minutes to emulsify the oil phase into the water solution. After milling is completed, mixing is continued with a 3" propeller at 350 rpm. The batch is held at 50° C. for 45 minutes, the temperature is increased to 75° C. in 30 minutes, held at 75° C. for 4 hours, heated to 95° C. in 30 minutes and held at 95° C. for 6 hours. The batch is then allowed to cool to room temperature.

Example 8

Spray Drying of Perfume Microcapsules

The microcapsules of Example 1 are pumped at a rate of 1 kg/hr into a co-current spray dryer (Niro Production Minor, 1.2 meter diameter) and atomized using a centrifugal wheel (100 mm diameter) rotating at 18,000 RPM. Dryer operating conditions are: air flow of 80 kg/hr, an inlet air temperature of 200 degrees Centigrade, an outlet temperature of 100 degrees Centigrade, dryer operating at a pressure of −150 millimeters of water vacuum. The dried powder is collected at the bottom of a cyclone. The collected microcapsules have an approximate particle diameter of 11 microns. The equipment used the spray drying process may be obtained from the following suppliers: IKA Werke GmbH & Co. KG, Janke and Kunkel—Str. 10, D79219 Staufen, Germany; Niro A/S Gladsaxevej 305, P.O. Box 45, 2860 Soeborg, Denmark and Watson-Marlow Bredel Pumps Limited, Falmouth, Cornwall, TR11 4RU, England.

Example 9

The microcapsules described in EXAMPLES 1-8 may be used as illustrated in the First Composition below at the indicated percentage.

|  | (% w/w) |
| --- | --- |
| Second Composition | |
| Ethanol (96%) | 74.88 |
| Fragrance | 14 |
| Water | 10.82 |
| Diethylamino Hydroxybenzol Hexyl Benzoate | 0.195 |
| Ethylhexyl Methoxycinnamate | 0.105 |
| First Composition | |
| Water | 92.5847 |
| Microcapsules | 6.0361 |
| Carbomer | 0.5018 |
| Phenoxyethanol | 0.2509 |
| Magnesium Chloride | 0.2456 |
| Sodium Hydroxide | 0.1254 |
| Disodium EDTA | 0.0836 |
| Polyvinyl alcohol | 0.0655 |
| Sodium Benzoate | 0.0409 |
| Potassium Sorbate | 0.0409 |
| Xanthan Gum | 0.0246 |

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An atomizing dispenser comprising:
   a first reservoir, the first reservoir comprising a first pump and a first composition;
   a second reservoir, the second reservoir comprising a second pump and a second composition;
   a first channel having a proximal end and a distal end;
   a second channel having a proximal end and a distal end;
   an exit orifice;
   a swirl chamber; and a
   lever assembly, the lever assembly comprising an actuator and a pivot providing structure;
   wherein the proximal end of the first channel is in liquid communication with the first pump and the distal end of the first channel is in liquid communication with the swirl chamber;
   wherein the proximal end of the second channel is in liquid communication with the second pump and the distal end of the second channel is in liquid communication with the swirl chamber;
   wherein the swirl chamber is in liquid communication with the exit orifice;
   wherein the lever assembly is operatively associated with the first pump and the second pump;
   wherein the first composition comprises a plurality of microcapsules having a fracture strength of from about 0.2 MPa to about 20 MPa and a median volume-weighted particle size of from about 2 microns to about 80 microns, a carrier which is water and a suspending agent and the second composition comprises a volatile solvent; and
   wherein said first composition is substantially free of said solvent and said second composition is substantially free of said microcapsules.

2. The dispenser of claim 1, wherein the lever assembly provides a mechanical advantage of from about 2 to about 3.

3. The dispenser of claim 1, wherein the lever assembly has a first length from the pivot providing structure to a force point and a second length from the force point to an end of a depressible area located on the actuator.

4. The dispenser of claim 3, wherein the ratio of the first length to the second length is from 10:1 to 1:10.

5. The dispenser of claim 3, wherein the first length and the second length have a combined length of from about 20 mm to about 120 mm.

6. The dispenser of claim 1, wherein the dispenser further comprises a protrusion capable of transferring a force from the actuator to the first and second pumps.

7. The dispenser of claim 6, wherein said protrusion is integral with the lever assembly.

8. The dispenser of claim 6, wherein said protrusion comprises a first engagement zone in communication with the first pump and a second engagement zone in communication with the second pump.

9. The dispenser of claim 6, wherein the dispenser further comprises a spreader operatively associated with the protrusion and the first and second pumps.

10. The dispenser of claim 9, wherein said protrusion is offset from the center point of the spreader.

11. The dispenser of claim 1, wherein the dispenser further comprises a premix chamber in liquid communication with the swirl chamber, the distal end of the first channel, and the distal end of the second channel.

12. The dispenser of claim 1, wherein the microcapsules comprise a core material and a shell encapsulating the core material; wherein the core material comprises a perfume oil.

13. The dispenser of claim 1, wherein the wherein the shell comprises a material selected from the group consisting of polyacrylates, polyethylenes, polyamides, polystyrenes, polyisoprenes, polycarbonates, polyesters, polyureas, polyurethanes, polyolefins, polysaccharides, epoxy resins, vinyl polymers, and combinations thereof.

* * * * *